United States Patent
Lopez et al.

(10) Patent No.: US 9,266,922 B2
(45) Date of Patent: Feb. 23, 2016

(54) ANTIGEN PEPTIDE AND USES THEREOF

(75) Inventors: Marc Lopez, Marseilles (FR); Daniel Olive, Marseilles (FR)

(73) Assignees: INSERM (Institut National de la Sante et de la Recherche Medicale), Paris (FR); Universite d'Aix Marseille, Marseilles (FR); Institut Jean Paoli & Irene Calmettes, Marseilles (FR)

( * ) Notice: Subject to any disclaimer, the term of this patent is extended or adjusted under 35 U.S.C. 154(b) by 0 days.

(21) Appl. No.: 14/122,937

(22) PCT Filed: May 31, 2012

(86) PCT No.: PCT/EP2012/060224
§ 371 (c)(1),
(2), (4) Date: Feb. 18, 2014

(87) PCT Pub. No.: WO2012/164004
PCT Pub. Date: Dec. 6, 2012

(65) Prior Publication Data
US 2014/0178394 A1 Jun. 26, 2014

(30) Foreign Application Priority Data
Jun. 1, 2011 (EP) .................................... 11305677

(51) Int. Cl.
| | |
|---|---|
| *C12N 5/10* | (2006.01) |
| *A61K 35/17* | (2015.01) |
| *C07K 7/06* | (2006.01) |
| *C07K 14/47* | (2006.01) |
| *C07K 14/78* | (2006.01) |
| *C07K 16/18* | (2006.01) |
| *C07K 14/725* | (2006.01) |
| *A61K 39/00* | (2006.01) |

(52) U.S. Cl.
CPC ............... *C07K 7/06* (2013.01); *C07K 14/4748* (2013.01); *C07K 14/78* (2013.01); *C07K 16/18* (2013.01); *A61K 35/17* (2013.01); *A61K 2039/5156* (2013.01)

(58) Field of Classification Search
None
See application file for complete search history.

(56) References Cited

U.S. PATENT DOCUMENTS

2010/0297006 A1* 11/2010 Raitano et al. ............... 424/1.49

FOREIGN PATENT DOCUMENTS

| WO | 2004/016799 A2 | 2/2004 |
| WO | 2006/014999 A2 | 2/2006 |

OTHER PUBLICATIONS

A_Geneseq ADK88377, 2004.*
Palmer et al (J. Immunol. 2004, 173: 72009-7216).*
Pittet et al (PNAS, 2007, 104(30): 12457-12461).*
Rossig and Brenner (Molec. Ther. 2004, 10(1): 5-18).*
Goodsell, D.S. (RCSB Protein Data Bank, 2005, 10.221-/rcsb_pdb/mom_2005_2).*
Celis et al (Mol. Immunol. 1994, 31(18): 1423-1430).*
Ochoa-Garay et al (Mol. Immunol. 1997, 34(3): 273-281).*
Karin et al (J. Exp. Med., 1994, 180, 2227-2237).*
Kalos and June (Immunity, 2013, 39: 49-60).*
Dermer (Bio/Technology, 1994, 12:320).*
Freshney (Culture of Animal Cells, A Manual of Basic Technique, Alan R. Liss, Inc., 1983, New York, p4).*
Zips et al (In Vivo, 2005, 19:1-7).*
Fabre-Lafay et al., "Nectin-4 is a new histological and serological tumor associated marker for breast cancer", BMC Cancer, May 2, 2007, p. 16PP, vol. 7, No. 73.

* cited by examiner

*Primary Examiner* — Michael Szperka
*Assistant Examiner* — Marianne Dibrino
(74) *Attorney, Agent, or Firm* — Whitham Curtis Christofferson & Cook, PC

(57) ABSTRACT

The invention relates to antigen peptide derived from the Nectin4 and its use for preventing and treating cancer.

2 Claims, 9 Drawing Sheets

Figure 1:
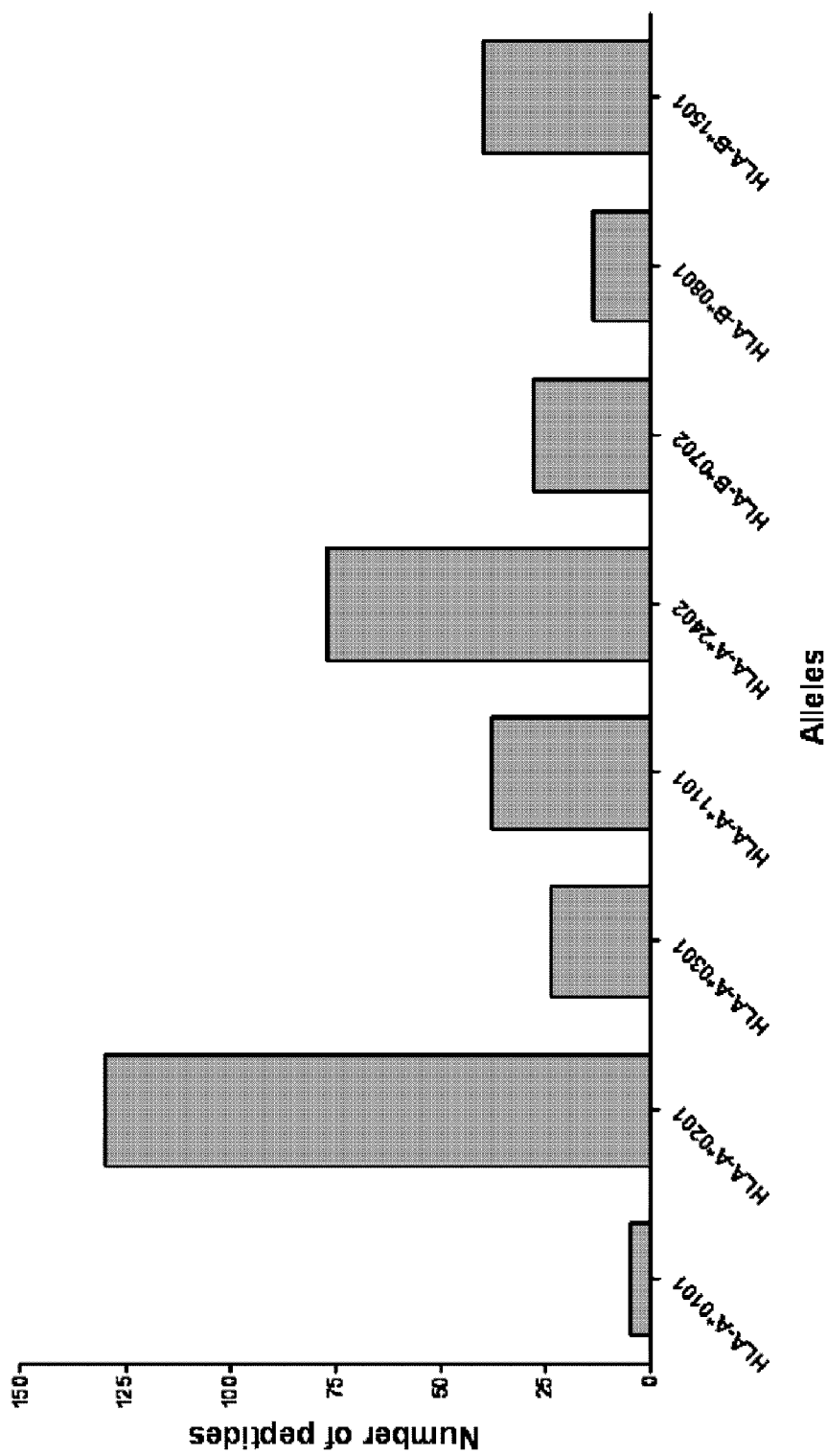

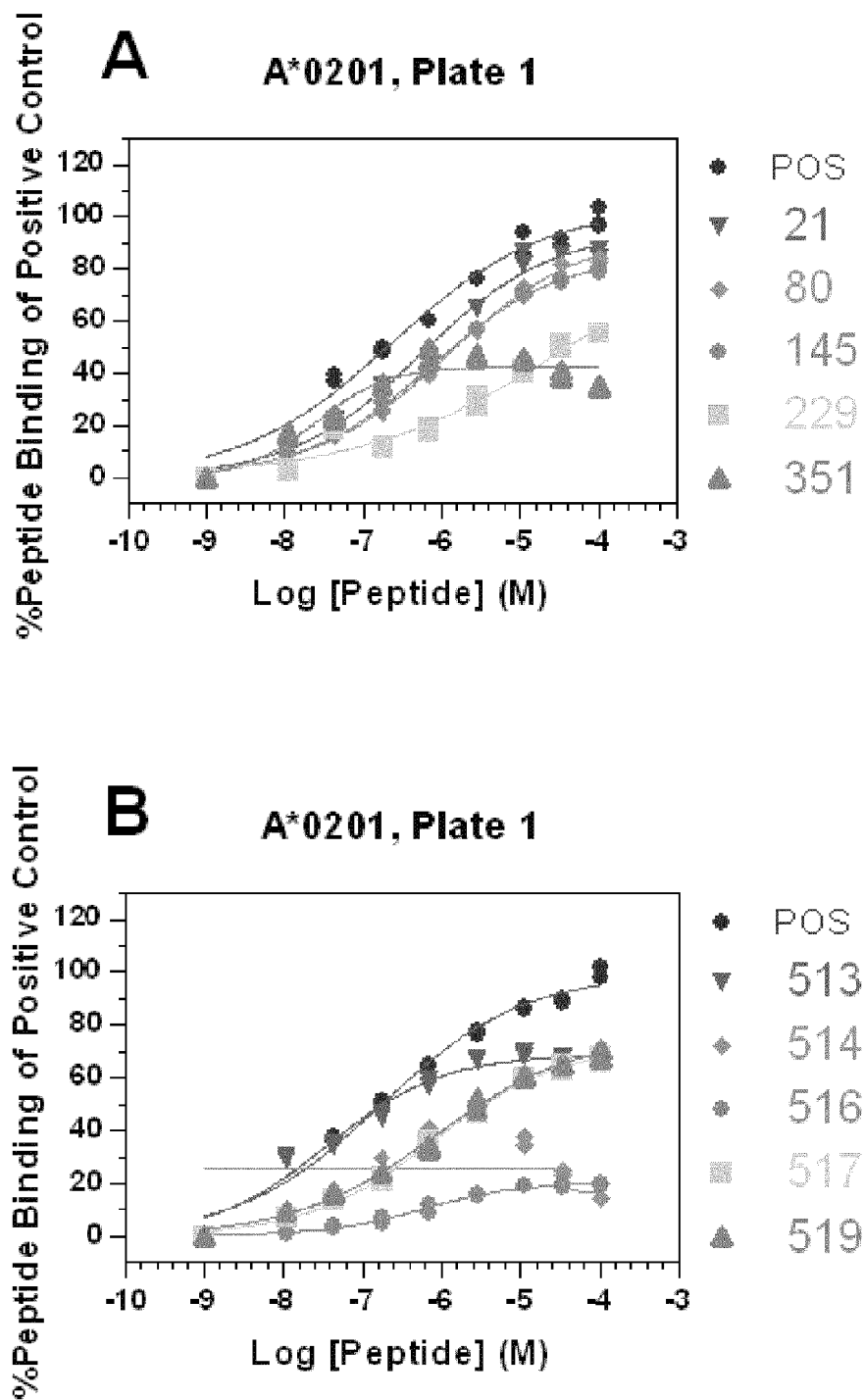
Figures 2 A and B

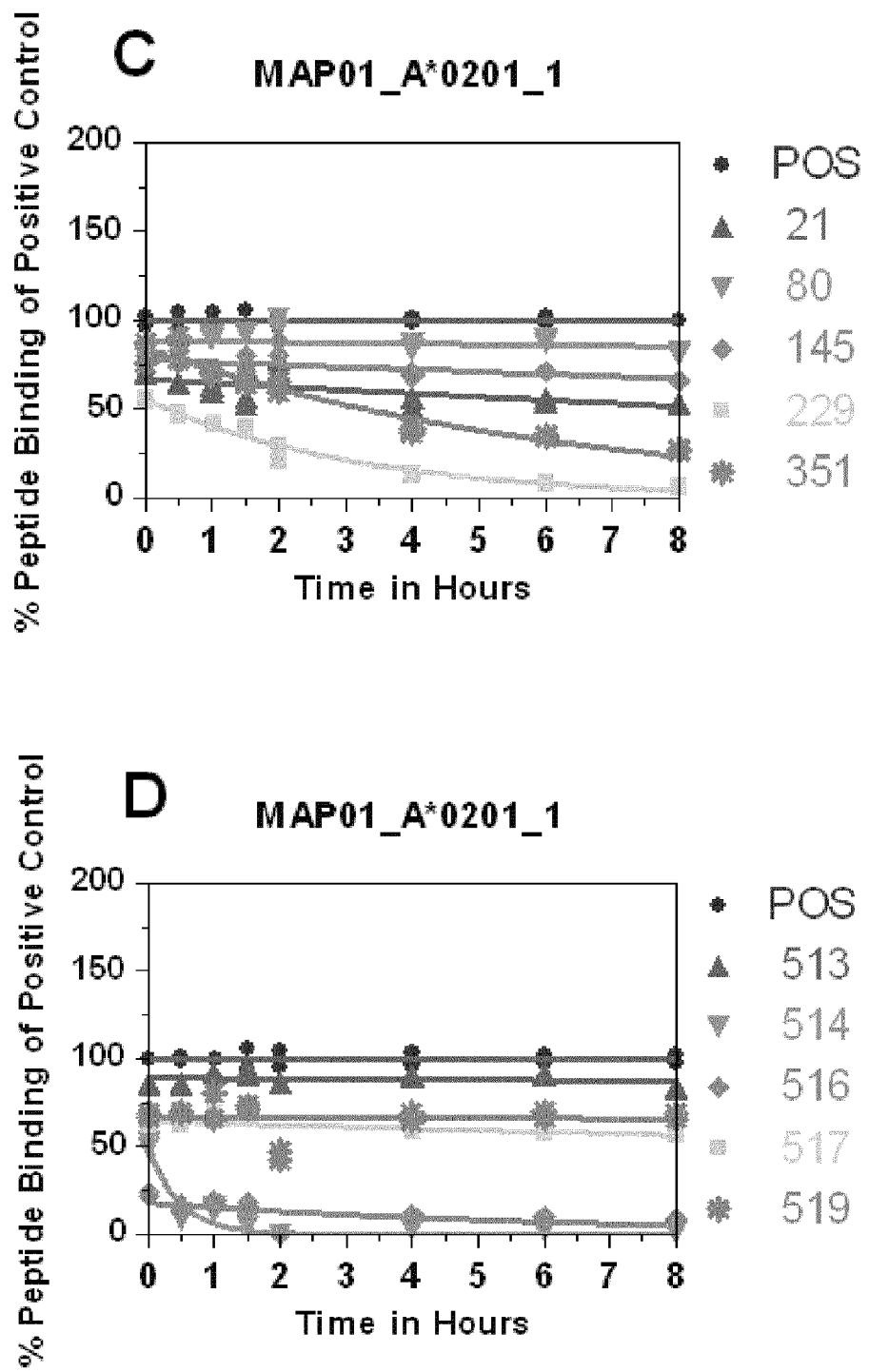
Figure 2 C and D

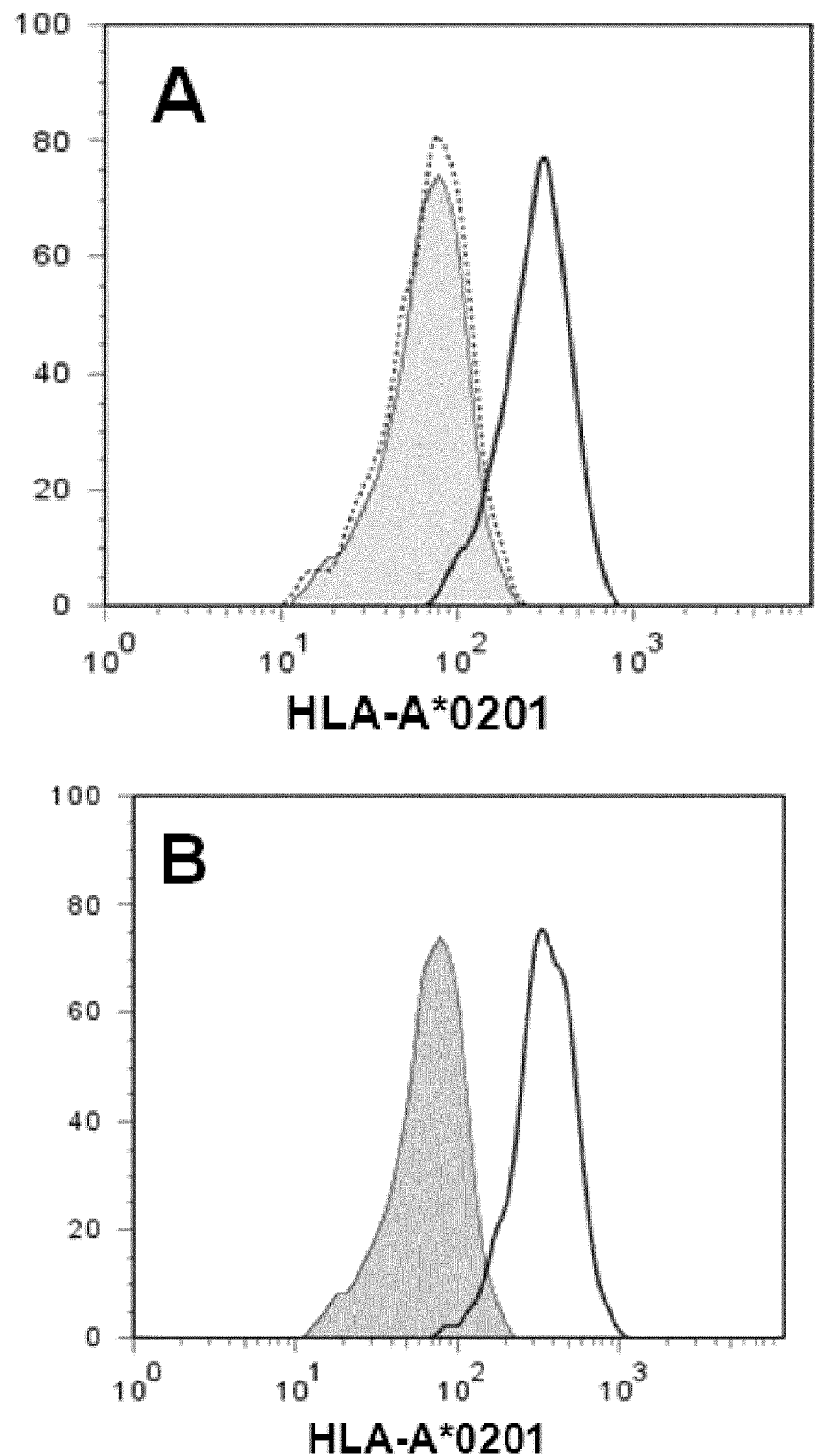
Figure 3 A and B

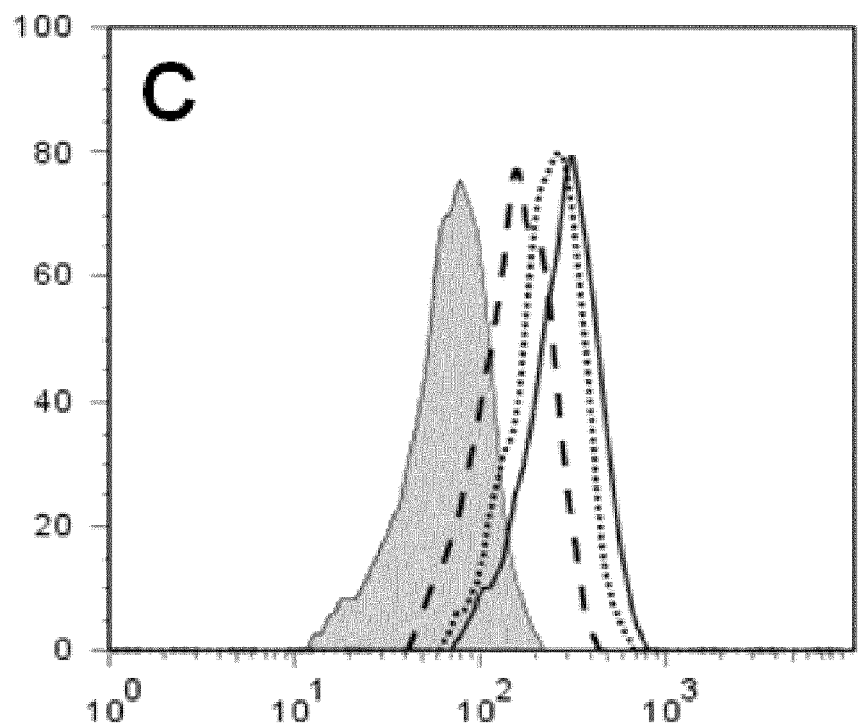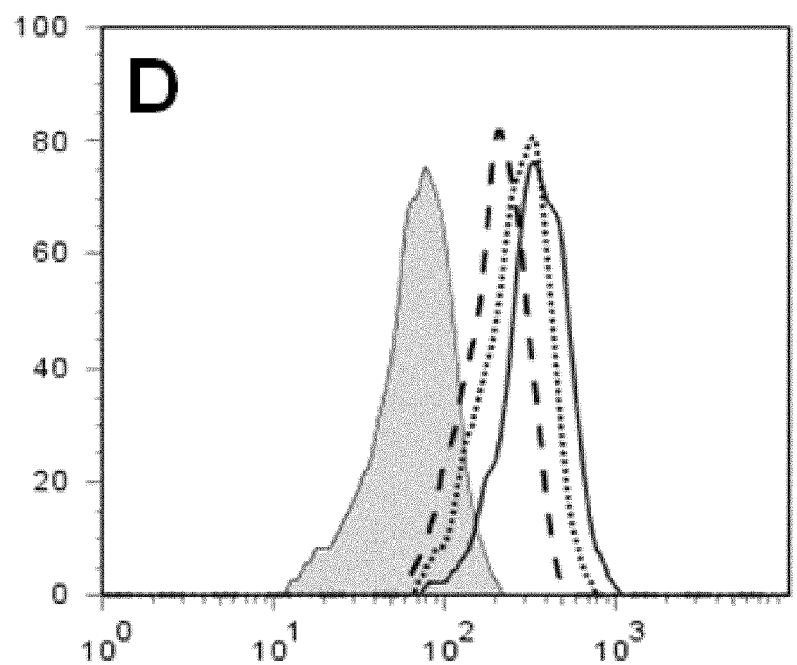
Figure 3 C and D

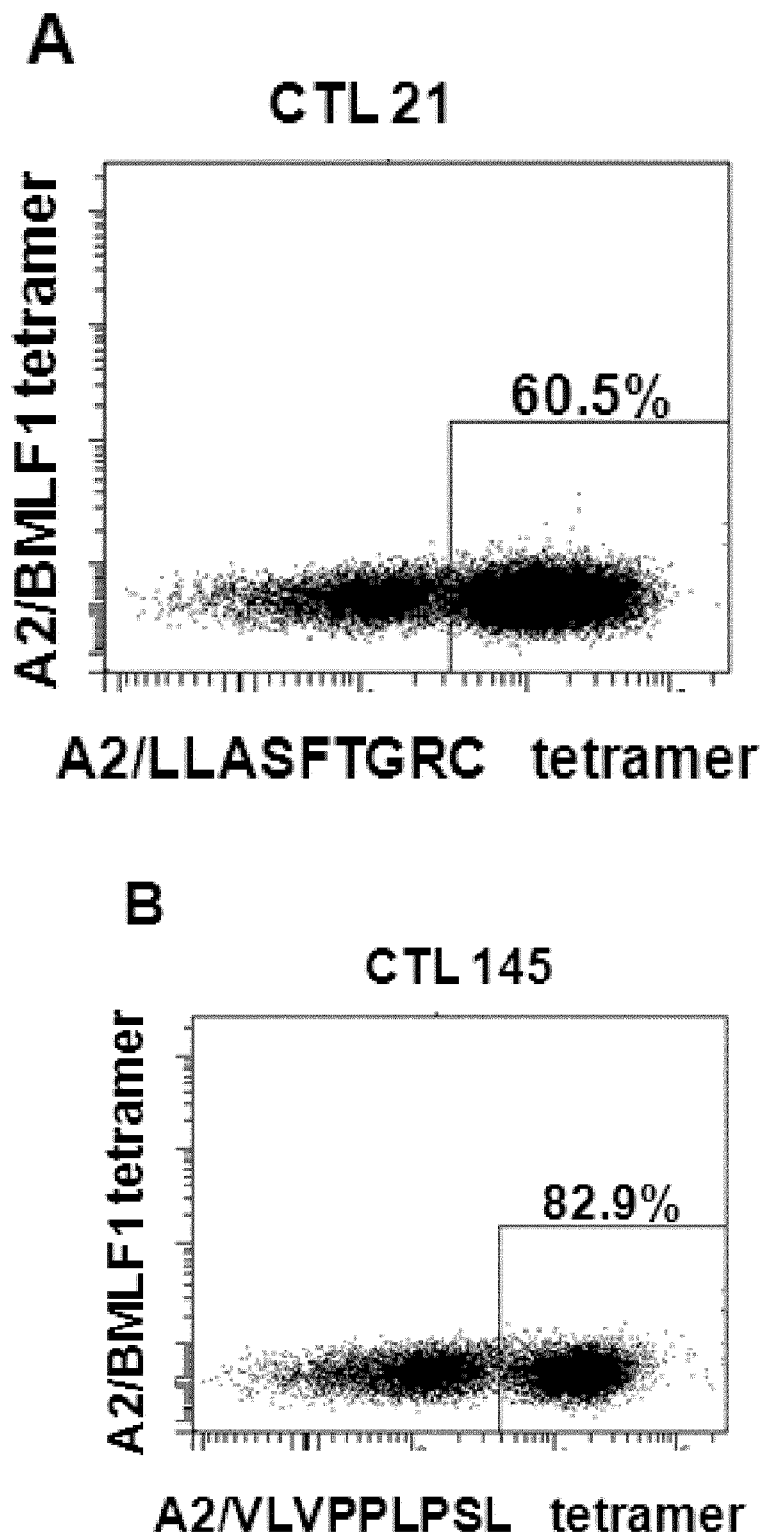
Figure 4 A and B

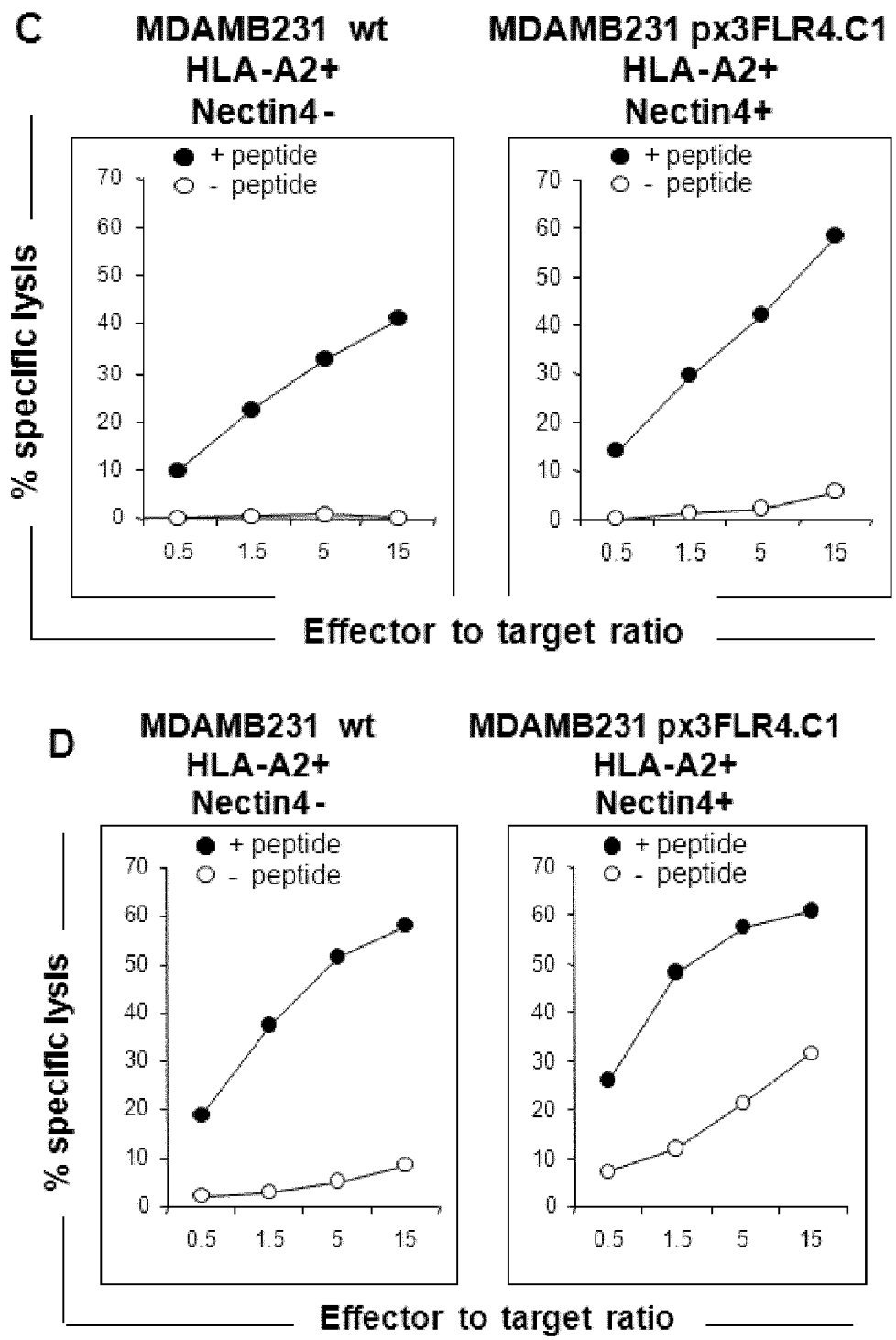
Figure 4 C and D

| Alleles | iTopia | Algorithms | | Alleles | iTopia | Algorithms | |
|---|---|---|---|---|---|---|---|
| | %Binding | SYFPEITHI | BIMAS | | %Binding | SYFPEITHI | BIMAS |
| HLA-A*0101 | 0 | 3 | 0.2 | HLA-A*2402 | 15.4 | 13 | 7.2 |
| HLA-A*0201 | 67 | 31 | 83.527 | HLA-B*0702 | 7.6 | 15 | 6 |
| HLA-A*0301 | 0.7 | 15 | 3.038 | HLA-A*0801 | 0.4 | 17 | 0.4 |
| HLA-A*1101 | 34.3 | 7 | 0.006 | HLA-B*1501 | 61 | 13 | 2.4 |

Figure 5 B

SEQUENCE LISTING

```
<160> NUMBER OF SEQ ID NOS: 33

<210> SEQ ID NO 1
<211> LENGTH: 3520
<212> TYPE: DNA
<213> ORGANISM: Homo sapiens

<400> SEQUENCE: 1
acctgttctg acctgctgag caggttccca ggtttctgcc gtcgttgttg gccacagcgt      60
gggaagcagc tctgggggag ctcggagctc ccgatcacgg cttcttgggg gtagctacgg     120
ctgggtgtgt agaacggggc cggggctggg gctgggtccc ctagtggaga cccaagtgcg     180
agaggcaaga actctgcagc ttcctgcctt ctgggtcagt tccttattca agtctgcagc     240
cggctcccag ggagatctcg gtggaacttc agaaacgctg ggcagtctgc ctttcaacca     300 tgccctgtc cctgggagcc gagatgtggg ggcctgaggc ctggctgctg ctgctgctac     360
tgctggcatc atttacaggc cggtgccccg cgggtgagct ggagacctca gacgtggtaa     420
ctgtggtgct gggccaggac gcaaaactgc cctgcttcta ccgaggggac tccggcgagc     480 aagtgggca agtggcatgg ctcgggtgg acgcgggcga aggcgcccag gaactagcgc     540
```

```
tactgcactc caaatacggg cttcatgtga gcccggctta cgagggccgc gtggagcagc      600
cgccgccccc acgcaaccc  ctggacggct cagtgctcct gcgcaacgca gtgcaggcgg      660
atgagggcga gtacgagtgc cgggtcagca ccttccccgc cggcagcttc caggcgcggc      720
tgcggctccg agtgctggtg cctcccctgc cctcactgaa tcctggtcca gcactagaag      780
agggccaggg cctgaccctg gcagcctcct gcacagctga gggcagccca gcccccagcg      840
tgacctggga cacggaggtc aaaggcacaa cgtccagccg ttccttcaag cactcccgct      900
ctgctgccgt cacctcagag ttccacttgg tgcctagccg cagcatgaat gggcagccac      960
tgacttgtgt ggtgtcccat cctggcctgc tccaggacca aaggatcacc cacatcctcc     1020
acgtgtcctt ccttgctgag gcctctgtga ggggcttga  agaccaaaat ctgtggcaca     1080
ttggcagaga aggagctatg ctcaagtgcc tgagtgaagg gcagccccct ccctcataca     1140
actggacacg gctggatggg cctctgccca gtggggtacg agtggatggg gacactttgg     1200
gctttccccc actgaccact gagcacacgc gcatctacgt ctgccatgtc agcaatgagt     1260
tctcctcaag ggattctcag gtcactgtgg atgttcttga ccccaggaa  gactctggga     1320
agcaggtgga cctagtgtca gcctcggtgg tggtggtggg tgtgatcgcc gcactcttgt     1380
tctgccttct ggtggtggtg gtggtgctca tgtcccgata ccatcggcgc aaggcccagc     1440
agatgaccca gaaatatgag gaggagctga ccctgaccag ggagaactcc atccggaggc     1500
tgcattccca tcacacggac cccaggagcc agccggagga gagtgtaggg ctgagagccg     1560
agggccaccc tgatagtctc aaggacaaca gtagctgctc tgtgatgagt gaagagcccg     1620
agggccgcag ttactccacg ctgaccacgg tgagggagat agaaacacag actgaactgc     1680
tgtctccagg ctctgggcgg gccgaggagg aggaagatca ggatgaaggc atcaaacagg     1740
ccatgaacca ttttgttcag gagaatggga ccctacgggc caagcccacg ggcaatggca     1800
tctacatcaa tgggcgggga cacctggtct gacccaggcc tgcctccctt ccctaggcct     1860
ggctccttct gttgacatgg gagattttag ctcatcttgg gggcctcctt aaacaccccc     1920
atttcttgcg gaagatgctc cccatcccac tgactgcttg accttacctt ccaacccttc     1980
tgttcatcgg gagggctcca ccaattgagt ctctcccacc atgcatgcag gtcactgtgt     2040
gtgtgcatgt gtgcctgtgt gagtgttgac tgactgtgtg tgtgtggagg ggtgactgtc     2100
cgtggagggg tgactgtgtc cgtggtgtgt attatgctgt catatcagag tcaagtgaac     2160
tgtggtgtat gtgccacggg atttgagtgg ttgcgtgggc aacactgtca gggtttggcg     2220
tgtgtgtcat gtggctgtgt gtgacctctg cctgaaaaag caggtatttt ctcagacccc     2280
agagcagtat taatgatgca gaggttggag gagagaggtg gagactgtgg ctcagaccca     2340
ggtgtgcggg catagctgga gctggaatct gcctccggtg tgagggaacc tgtctcctac     2400
cacttcggag ccatgggggc aagtgtgaag cagccagtcc ctgggtcagc cagaggcttg     2460
aactgttaca gaagccctct gccctctggt ggcctctggg cctgctgcat gtacatattt     2520
tctgtaaata tacatgcgcc gggagcttct tgcaggaata ctgctccgaa tcactttaa     2580
tttttttctt tttttttct  tgcccttttcc attagttgta ttttttattt attttttatt     2640
ttatttttt  ttagagatgg agtctcacta tgttgctcag gctggccttg aactcctggg     2700
ctcaagcaat cctcctgcct cagcctccct agtagctggg actttaagtg tacaccactg     2760
tgcctgcttt gaatccttta cgaagagaaa aaaaaatta  agaaagcct  ttagatttat     2820
ccaatgttta ctactgggat tgcttaaagt gaggcccctc caacaccagg gggttaattc     2880
```

-continued

| | |
|---|---|
| ctgtgattgt gaaaggggct acttccaagg catcttcatg caggcagccc cttgggaggg | 2940 |
| cacctgagag ctggtagagt ctgaaattag ggatgtgagc ctcgtggtta ctgagtaagg | 3000 |
| taaaattgca tccaccattg tttgtgatac cttagggaat tgcttggacc tggtgacaag | 3060 |
| ggctcctgtt caatagtggt gttggggaga gagagagcag tgattataga ccgagagagt | 3120 |
| aggagttgag gtgaggtgaa ggaggtgctg ggggtgagaa tgtcgccttt cccctgggt | 3180 |
| tttggatcac taattcaagg ctcttctgga tgtttctctg ggttggggct ggagttcaat | 3240 |
| gaggtttatt tttagctggc ccacccagat acactcagcc agaataccta gatttagtac | 3300 |
| ccaaactctt cttagtctga aatctgctgg atttctggcc taagggagag gctcccatcc | 3360 |
| ttcgttcccc agccagccta ggacttcgaa tgtggagcct gaagatctaa gatcctaaca | 3420 |
| tgtacatttt atgtaaatat gtgcatattt gtacataaaa tgatattctg ttttaaata | 3480 |
| aacagacaaa acttgttctg tcaaaaaaaa aaaaaaaaa | 3520 |

<210> SEQ ID NO 2
<211> LENGTH: 9
<212> TYPE: PRT
<213> ORGANISM: Homo sapiens

<400> SEQUENCE: 2

Val Leu Val Pro Pro Leu Pro Ser Leu
1               5

<210> SEQ ID NO 3
<211> LENGTH: 9
<212> TYPE: PRT
<213> ORGANISM: Homo sapiens

<400> SEQUENCE: 3

Asn Leu Ser Ala Ser Val Ala Thr Val
1               5

<210> SEQ ID NO 4
<211> LENGTH: 9
<212> TYPE: PRT
<213> ORGANISM: Homo sapiens

<400> SEQUENCE: 4

Ser Leu Leu Met Trp Ile Thr Gln Val
1               5

<210> SEQ ID NO 5
<211> LENGTH: 9
<212> TYPE: PRT
<213> ORGANISM: Homo sapiens

<400> SEQUENCE: 5

Leu Tyr Val Asp Ser Leu Phe Phe Leu
1               5

<210> SEQ ID NO 6
<211> LENGTH: 9
<212> TYPE: PRT
<213> ORGANISM: Homo sapiens

<400> SEQUENCE: 6

Lys Val Ala Glu Leu Val His Phe Leu
1               5

<210> SEQ ID NO 7

```
<211> LENGTH: 9
<212> TYPE: PRT
<213> ORGANISM: Homo sapiens

<400> SEQUENCE: 7

Ala Ser Ser Thr Leu Tyr Leu Val Phe
1               5

<210> SEQ ID NO 8
<211> LENGTH: 9
<212> TYPE: PRT
<213> ORGANISM: Homo sapiens

<400> SEQUENCE: 8

Gly Leu Tyr Asp Gly Met Glu His Leu
1               5

<210> SEQ ID NO 9
<211> LENGTH: 9
<212> TYPE: PRT
<213> ORGANISM: Homo sapiens

<400> SEQUENCE: 9

Ala Leu Lys Asp Val Glu Glu Arg Val
1               5

<210> SEQ ID NO 10
<211> LENGTH: 9
<212> TYPE: PRT
<213> ORGANISM: Homo sapiens

<400> SEQUENCE: 10

Tyr Met Asp Gly Thr Met Ser Gln Val
1               5

<210> SEQ ID NO 11
<211> LENGTH: 9
<212> TYPE: PRT
<213> ORGANISM: Homo sapiens

<400> SEQUENCE: 11

Val Leu Pro Asp Val Phe Ile Arg Cys
1               5

<210> SEQ ID NO 12
<211> LENGTH: 9
<212> TYPE: PRT
<213> ORGANISM: Homo sapiens

<400> SEQUENCE: 12

His Ile Leu His Val Ser Phe Leu Ala
1               5

<210> SEQ ID NO 13
<211> LENGTH: 9
<212> TYPE: PRT
<213> ORGANISM: Homo sapiens

<400> SEQUENCE: 13

Val Ile Ala Ala Leu Leu Phe Cys Leu
1               5

<210> SEQ ID NO 14
<211> LENGTH: 9
<212> TYPE: PRT
```

```
<213> ORGANISM: Homo sapiens

<400> SEQUENCE: 14

Gly Val Ile Ala Ala Leu Leu Phe Cys
1               5

<210> SEQ ID NO 15
<211> LENGTH: 9
<212> TYPE: PRT
<213> ORGANISM: Homo sapiens

<400> SEQUENCE: 15

Ala Leu Leu His Ser Lys Tyr Gly Leu
1               5

<210> SEQ ID NO 16
<211> LENGTH: 9
<212> TYPE: PRT
<213> ORGANISM: Homo sapiens

<400> SEQUENCE: 16

Val Val Val Gly Val Ile Ala Ala Leu
1               5

<210> SEQ ID NO 17
<211> LENGTH: 9
<212> TYPE: PRT
<213> ORGANISM: Homo sapiens

<400> SEQUENCE: 17

Leu Leu Ala Ser Phe Thr Gly Arg Cys
1               5

<210> SEQ ID NO 18
<211> LENGTH: 9
<212> TYPE: PRT
<213> ORGANISM: Homo sapiens

<400> SEQUENCE: 18

Ala Leu Leu Phe Cys Leu Leu Val Val
1               5

<210> SEQ ID NO 19
<211> LENGTH: 9
<212> TYPE: PRT
<213> ORGANISM: Homo sapiens

<400> SEQUENCE: 19

Ser Ala Ser Val Val Val Val Gly Val
1               5

<210> SEQ ID NO 20
<211> LENGTH: 9
<212> TYPE: PRT
<213> ORGANISM: Homo sapiens

<400> SEQUENCE: 20

Ser Met Asn Gly Gln Pro Leu Thr Cys
1               5

<210> SEQ ID NO 21
<211> LENGTH: 9
<212> TYPE: PRT
<213> ORGANISM: Homo sapiens
```

<400> SEQUENCE: 21

Leu Leu Phe Cys Leu Leu Val Val Val
1               5

<210> SEQ ID NO 22
<211> LENGTH: 9
<212> TYPE: PRT
<213> ORGANISM: Homo sapiens

<400> SEQUENCE: 22

Ala Met Leu Lys Cys Leu Ser Glu Gly
1               5

<210> SEQ ID NO 23
<211> LENGTH: 9
<212> TYPE: PRT
<213> ORGANISM: Homo sapiens

<400> SEQUENCE: 23

Phe Gln Ala Arg Leu Arg Leu Arg Val
1               5

<210> SEQ ID NO 24
<211> LENGTH: 9
<212> TYPE: PRT
<213> ORGANISM: Homo sapiens

<400> SEQUENCE: 24

Leu Leu Leu Leu Ala Ser Phe Thr Gly
1               5

<210> SEQ ID NO 25
<211> LENGTH: 9
<212> TYPE: PRT
<213> ORGANISM: Homo sapiens

<400> SEQUENCE: 25

Leu Val Ser Ala Ser Val Val Val Val
1               5

<210> SEQ ID NO 26
<211> LENGTH: 9
<212> TYPE: PRT
<213> ORGANISM: Homo sapiens

<400> SEQUENCE: 26

Ala Ala Leu Leu Phe Cys Leu Leu Val
1               5

<210> SEQ ID NO 27
<211> LENGTH: 9
<212> TYPE: PRT
<213> ORGANISM: Homo sapiens

<400> SEQUENCE: 27

Gly Thr Ser Asp Val Val Thr Val Val
1               5

<210> SEQ ID NO 28
<211> LENGTH: 9
<212> TYPE: PRT
<213> ORGANISM: Homo sapiens

<400> SEQUENCE: 28

```
Asp Gln Asn Leu Trp His Ile Gly Arg
1               5

<210> SEQ ID NO 29
<211> LENGTH: 9
<212> TYPE: PRT
<213> ORGANISM: Homo sapiens

<400> SEQUENCE: 29

Phe Leu Ala Glu Ala Ser Val Arg Gly
1               5

<210> SEQ ID NO 30
<211> LENGTH: 9
<212> TYPE: PRT
<213> ORGANISM: Homo sapiens

<400> SEQUENCE: 30

Ala Val Thr Ser Glu Phe His Leu Val
1               5

<210> SEQ ID NO 31
<211> LENGTH: 9
<212> TYPE: PRT
<213> ORGANISM: Homo sapiens

<400> SEQUENCE: 31

Arg Ser Tyr Ser Thr Leu Thr Thr Val
1               5

<210> SEQ ID NO 32
<211> LENGTH: 9
<212> TYPE: PRT
<213> ORGANISM: Homo sapiens

<400> SEQUENCE: 32

Ile Leu His Val Ser Phe Leu Ala Glu
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic peptide

<400> SEQUENCE: 33

Val Ser Asp Gly Gly Pro Asn Leu Tyr
1               5
```

ANTIGEN PEPTIDE AND USES THEREOF

FIELD OF THE INVENTION

The invention relates to antigen peptide derived from the Nectin4 and its use for preventing and treating cancer.

BACKGROUND OF THE INVENTION

Over the recent years, the understanding of tumor biology processes lead to the development of targeted therapies like tyrosine kinase inhibitors or monoclonal antibodies. Recent results obtained with monoclonal antibodies validated the immunotherapy approach. Induction of immunity by cancer vaccines is thought to induce immune memory and thereby prevent tumor development. Many immunotherapeutic approaches are aimed to stimulate anti tumor CD8+ CTL responses. New cell surface expressed tumor associated antigens (TAA) that are shared among different tumors and not expressed in normal tissues are attractive candidates for used in vaccines.

The inventors recently described a new tumor associated antigen named Nectin4 [S. Fabre-Lafay et al., 2007] which have been described as a new TAA in 50%, 49% and 86% of breast, ovarian and lung carcinomas respectively. Moreover, a soluble form of Nectin4 is found in sera of patients and Nectin4 expression is mainly found in tumors with adverse prognosis. These characteristics assigned Nectin4 as a potent candidate for used in vaccination.

Nectin4 is already known in cancer. For example, patent application WO2004016799 discloses 9mer peptides obtainable from the Nectin4 sequence and their possible use as vaccine against cancer. However, this patent application doesn't disclose experimental results and doesn't give any information about relevant peptides.

SUMMARY OF THE INVENTION

In order to identify new Nectin4 antigens, the inventors have done a multiplex approach aiming to select the most relevant peptide antigen candidate using a combination of biochemical (iTOPIA Epitope Discovery System which includes MHC class I monomer coated plates representing 8 alleles (the Class I monomers are A*0101, A*0201, A*0301, A*1101, A*2402, B*0702, B*0801 and B*1501)), cellular (CEM-T2 cell line) and algorithmic (SYFPEITHI)-based methods.

The critical steps of this approach are: 1) peptide sequence; 2) demonstration of appropriate processing of the peptide inside cell; 3) peptide binding to the relevant HLA class 1 or Class 2 molecule; 4) recognition by T cell receptor.

Based on the Nectin4 sequence, the inventors have synthesized all the relevant 9-mer peptides (502). Among all the candidate peptides, they have identified peptides bound with high avidity to HLA-A2, recognized by T cells and finally efficiently processed and presented by tumor cells.

The study led the inventors to identify a new antigen peptide (SEQ ID NO: 2) named N4-145 that are recognized by HLA-A*0201-restricted CTL.

Thus, the invention relates to an antigen peptide comprising the amino acids motif:

VLVPPLPSL (SEQ ID NO 2), wherein the peptide may differ from 1, 2 or 3 aminoacids.

Another object of the invention relates to an expression vector comprising a nucleic acid sequence encoding an antigen peptide according to the invention.

Another object of the invention relates to a host cell comprising an expression vector according to the invention.

Another object of the invention relates to an antibody or fragment thereof that binds to the antigen peptide according to the invention.

Another object of the invention relates to an MHC/peptide multimer comprising an antigen peptide according to the invention.

Another object of the invention relates to an immunising composition comprising
 (a) at least one antigen peptide according to the invention or
 (b) at least one expression vector according to the invention, or
 (c) at least one host cell according to the invention, or
 (d) at least one antibody according to the invention, or
 (e) at least one nucleic acid sequence that encodes at least one antigen peptide according to the invention.

Another object of the invention relates to a T lymphocyte that recognizes specifically an antigen peptide according to the invention.

Another object of the invention relates to a composition for adoptive therapy comprising T lymphocytes according to the invention.

Another object of the invention relates to a method for producing said T lymphocytes according to the invention, said method comprising the steps of:
 (a) stimulating PBMCs or tumor infiltrating lymphocytes obtained from a subject with at least one antigen peptide according to the invention,
 (b) enriching the population of T lymphocytes specific for the antigen peptide(s) used in (a),
 (c) optionally cloning said population of T lymphocytes specific for the antigen peptide(s) used in (a).

Another object of the invention relates to a method for monitoring a cancer in a subject in need thereof, comprising determining the frequency of T lymphocytes that recognize specifically an antigen peptide according to the invention.

DETAILED DESCRIPTION OF THE INVENTION

Definitions

Throughout the specification, several terms are employed and are defined in the following paragraphs.

As used herein, the term "Nectin4" denotes a new tumor associated antigen which is a cell surface expressed adhesion molecule and belongs to the nectin family [N. Reymond, et al., 2001 and S. Fabre-Lafay, et al., 2005]. Nectins are widely expressed in tissues and play a key role in different biological processes during development and adult life [Y. Takai et al., 2003, Y. Takai et al., 2008, N. Reymond et al., 2004, Y. Takai et al., 2008, and Fournier et al 2010 (med sciences)]. Nectins have been involved in different pathological processes in humans [D. Pende et al., 2005, M. Kuramochi et al., 2001 and F. Brancati et al., 2010]. An exemplary sequence for human nectin4 gene is deposited in the database under accession number AF426163 (SEQ ID NO:1).

As used herein, the term "peptide" refers to an amino acid sequence having less than 50 amino acids. As used herein, the term "peptide" encompasses amino acid sequences having less than 50 amino acids, less than 40 amino acids, less than 30 amino acids, less than 25 amino acids, less than 20 amino acids, less than 15 amino acids or less than 10 amino acids.

As used herein, the term "antibody" refers to a protein capable of specifically binding an antigen, typically and preferably by binding an epitope or antigenic determinant or said antigen. The term "antibody" also includes recombinant proteins comprising the binding domains, as well as variants and fragments of antibodies. Examples of fragments of antibodies include Fv, Fab, Fab', F(ab')2, dsFv, scFv, sc(Fv)$_2$, diabodies and multispecific antibodies formed from antibody fragments.

"Function-conservative variants" as used herein refer to those in which a given amino acid residue in a protein or enzyme has been changed (inserted, deleted or substituted) without altering the overall conformation and function of the polypeptide. Such variants include protein having amino acid alterations such as deletions, insertions and/or substitutions. A "deletion" refers to the absence of one or more amino acids in the protein. An "insertion" refers to the addition of one or more of amino acids in the protein. A "substitution" refers to the replacement of one or more amino acids by another amino acid residue in the protein. Typically, a given amino acid is replaced by an amino acid with one having similar properties (such as, for example, polarity, hydrogen bonding potential, acidic, basic, hydrophobic, aromatic, and the like). Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide which has at least 60% amino acid identity as determined by BLAST or FASTA algorithms, preferably at least 75%, more preferably at least 85%, still preferably at least 90%, and even more preferably at least 95%, and which has the same or substantially similar properties or functions as the native or parent protein to which it is compared. Two amino acid sequences are "substantially homologous" or "substantially similar" when greater than 80%, preferably greater than 85%, preferably greater than 90% of the amino acids are identical, or greater than about 90%, preferably greater than 95%, are similar (functionally identical) over the whole length of the shorter sequence. Preferably, the similar or homologous sequences are identified by alignment using, for example, the GCG (Genetics Computer Group, Program Manual for the GCG Package, Version 7, Madison, Wis.) pileup program, or any of sequence comparison algorithms such as BLAST, FASTA, etc.

The term "Major Histocompatibility Complex" (MHC) is a generic designation meant to encompass the histo-compatibility antigen systems described in different species including the human leucocyte antigens (HLA).

The term "breast cancer" as used herein includes, but is not limited to, all types of breast cancers at all stages of progression like metastatic breast cancer or breast carcinomas.

The term "ovarian cancer" as used herein includes, but is not limited to, all types of ovarian cancers at all stages of progression like metastatic ovarian cancer or ovarian carcinomas.

The term "lung cancer" as used herein includes, but is not limited to all types of lung cancers at all stages of progression like lung carcinomas metastatic lung cancer, non-small cell lung carcinomas or Small cell lung carcinoma.

The term "treating" a disorder or a condition refers to reversing, alleviating or inhibiting the process of one or more symptoms of such disorder or condition. The term "preventing" a disorder or condition refers to preventing one or more symptoms of such disorder or condition.

As used herein, the term "subject" denotes a mammal, such as a rodent, a feline, a canine, and a primate. Preferably a subject according to the invention is a human.

A "therapeutically effective amount" as used herein is intended for a minimal amount of active agent which is necessary to impart therapeutic benefit to a subject. For example, a "therapeutically effective amount of the active agent" to a subject is an amount of the active agent that induces, ameliorates or causes an improvement in the pathological symptoms, disease progression, or physical conditions associated with the disease affecting the subject.

The term "adjuvant" as used herein refers to a compound or a mixture that may be non-immunogenic when administered in the host alone, but that augments the host's immune response to an antigen when administered conjointly with that antigen.

Peptide and Uses Thereof

A first object of the invention relates to an antigen peptide comprising the amino acids motif:

VLVPPLPSL (SEQ ID NO: 2)

wherein the peptide may differ from 1, 2 or 3 aminoacids.

In one embodiment of the invention, by "antigen peptide" is meant a peptide capable of binding to HLA molecule and causing a cellular or humoral response in a subject.

In a preferred embodiment of the invention, said antigen peptide may comprise a specific motif such that the polypeptide binds an HLA molecule and induces a CTL response.

In another preferred embodiment of the invention, said antigen peptide may comprise a specific motif such that the polypeptide binds an HLA molecule and induces a helper T cell response.

In another embodiment of the invention, said antigen peptides as described here above are HLA-A*0201 restricted.

In one embodiment of the invention, said antigen peptide is an amino acid sequence of less than 50 amino acids long that comprises the amino acid motif SEQ ID NO: 2 as defined here above.

In another embodiment of the invention, said antigen peptide is an amino acid sequence of less than 45 amino acids long that comprises the amino acid motif SEQ ID NO: 2 as defined here above.

In another embodiment of the invention, said antigen peptide is an amino acid sequence of less than 40 amino acids long that comprises the amino acid motif SEQ ID NO: 2 as defined here above.

In another embodiment of the invention, said antigen peptide is an amino acid sequence of less than 30 amino acids long that comprises the amino acid motif SEQ ID NO: 2 as defined here above.

In another embodiment of the invention, said antigen peptide is an amino acid sequence of less than 20 amino acids long that comprises the amino acid motif SEQ ID NO: 2 as defined here above.

In another embodiment of the invention, said antigen peptide is an amino acid sequence of less than 15 amino acids long that comprises the amino acid motif SEQ ID NO: 2 as defined here above.

In another embodiment of the invention, said antigen peptide is an amino acid sequence of 10 or 11 amino acids long that comprises the amino acid motif SEQ ID NO: 2 as defined here above.

The invention also encompasses peptides that are function-conservative variants of antigen peptides comprising SEQ ID NO: 2 as described here above.

Typically, the invention encompasses peptides substantially identical to antigen peptides comprising SEQ ID NO: 2 in which one or more residues have been conservatively substituted with a functionally similar residue and which displays the functional aspects of the antigen peptides comprising SEQ ID NO: 2 as described here above, i.e. being still able to bind to an HLA molecule in substantially the same way as a peptide consisting of the given amino acid sequence.

Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid or another.

The term "conservative substitution" also includes the use of a chemically derivatized residue in place of a non-derivatized residue. "Chemical derivative" refers to a subject peptide having one or more residues chemically derivatized by reaction of a functional side group. Examples of such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-imbenzylhistidine. Chemical derivatives also include peptides which contain one or more naturally-occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine.

According to the invention, the antigen peptides of the invention can be obtained by synthesizing the peptides according to the method for peptide synthesis known in the art.

In another embodiment, the antigen peptides of the invention may be incorporated into polytopes. Two or more peptides of the invention can be joined together directly, or via the use of flanking sequences. Thompson et al., Proc. Natl. Acad. Sci. USA 92 (13): 5845-5849 (1995), teaches the direct linkage of relevant epitopic sequences. The use of polytopes as vaccines is well known. See, e.g. Gilbert et al., Nat. Biotechnol. 15 (12): 1280-1284 (1997); Thomson et al., supra; Thomson et al., J. Immunol. 157 (2): 822-826 (1996); Tam et al., J. Exp. Med. 171 (1): 299-306 (1990), all of which are incorporated by reference. The Tam et al. reference in particular shows that polytopes, when used in a mouse model, are useful in generating both antibody and protective immunity.

In another embodiment, the antigen peptide according to the invention may be use in the prevention or treatment of cancer.

In a preferred embodiment, cancer may be selected from the group consisting of breast, ovarian or lung cancer.

Vectors, Recombinant Host Cells and Uses Thereof

Another object of the invention is an expression vector comprising a nucleic acid sequence encoding an amino sequence comprising SEQ ID NO: 2 as described here above.

In one embodiment of the invention, said expression vector comprises the nucleic acid sequence corresponding to the open reading frame 433 to 459 of SEQ ID NO: 1.

According to the invention, expression vectors suitable for use in the invention may comprise at least one expression control element operationally linked to the nucleic acid sequence. The expression control elements are inserted in the vector to control and regulate the expression of the nucleic acid sequence. Examples of expression control elements include, but are not limited to, lac system, operator and promoter regions of phage lambda, yeast promoters and promoters derived from polyoma, adenovirus, retrovirus, lentivirus or SV40. Additional preferred or required operational elements include, but are not limited to, leader sequence, termination codons, polyadenylation signals and any other sequences necessary or preferred for the appropriate transcription and subsequent translation of the nucleic acid sequence in the host system. It will be understood by one skilled in the art that the correct combination of required or preferred expression control elements will depend on the host system chosen. It will further be understood that the expression vector should contain additional elements necessary for the transfer and subsequent replication of the expression vector containing the nucleic acid sequence in the host system. Examples of such elements include, but are not limited to, origins of replication and selectable markers. It will further be understood by one skilled in the art that such vectors are easily constructed using conventional methods or commercially available.

Another object of the invention is a host cell comprising an expression vector as described here above.

According to the invention, examples of host cells that may be used are eukaryote cells, such as animal, plant, insect and yeast cells and prokaryotes cells, such as *E. coli*. The means by which the vector carrying the gene may be introduced into the cells include, but are not limited to, microinjection, electroporation, transduction, or transfection using DEAE-dextran, lipofection, calcium phosphate or other procedures known to one skilled in the art.

In a preferred embodiment, eukaryotic expression vectors that function in eukaryotic cells are used. Examples of such vectors include, but are not limited to, viral vectors such as retrovirus, adenovirus, adeno-associated virus, herpes virus, vaccinia virus, poxvirus, poliovirus; lentivirus, bacterial expression vectors, plasmids, such as pcDNA3 or the baculovirus transfer vectors. Preferred eukaryotic cell lines include, but are not limited to, COS cells, CHO cells, HeLa cells, NIH/3T3 cells, 293 cells (ATCC# CRL1573), T2 cells, dendritic cells, or monocytes.

Antibodies and Uses Thereof

Another object of the invention relates to an antibody or fragment thereof that binds to the antigen peptide according to invention.

In one embodiment of the invention, said antibody or fragment thereof binds to the peptide of SEQ ID NO: 2.

In one embodiment of the invention, said antibody is monoclonal. In another embodiment of the invention, said antibody is polyclonal. Such antibodies may be easily prepared, for example, according to the method described in "Antibodies: A laboratory manual", Lane H. D. et al. eds, Cold Spring Harbor Laboratory Press, New York, 1989 or Antibody Engineering: Methods and Protocols, 2003, Benny K. Lo.

MHC/Peptide Multimer

Another object of the invention is a MHC/peptide multimer comprising an antigen peptide as described here above.

According to the invention, said MHC/peptide multimer include, but are not limited to, a MHC/peptide dimer, trimer, tetramer or pentamer.

In one embodiment of the invention, said MHC/peptide multimer is a HLA-A*0201/peptide multimer.

Methods for obtaining MHC/peptide tetramers are described in WO96/26962 and WO01/18053, which are incorporated by reference.

In one embodiment of the invention, said MHC/peptide multimer can be used to visualise T cell populations that are specific for the complex HLA-A*0201/antigen peptide as described here above.

In another embodiment of the invention, said MHC/peptide multimer can be used for the detection and/or isolation by screening (in flow cytometry or by immunomagnetic screening) of T cell population that are specific for a complex HLA/antigen peptide as described here above.

In another embodiment of the invention, said HLA-A*0201/peptide multimer can be used for the detection and/or isolation by screening (in flow cytometry or by immunomagnetic screening) of T cell population that are specific for a complex HLA-A*201/antigen peptide as described here above.

Another object of the invention is beads coated with MHC/peptide multimers as described here above.

Immunising Composition

Another object of the invention is an immunising composition comprising
(a) at least one antigen peptide as described here above or
(b) at least one expression vector as described here above, or
(c) at least one host cell as described here above, or
(d) at least one antibody as described here above, or
(e) at least one nucleic acid sequence that encodes at least one antigen peptide as described here above.

In one embodiment, said immunising composition comprises the antigen peptide N4-145 having the sequence SEQ ID NO: 2.

The prophylactic administration of the immunising composition of the invention should serve to prevent or attenuate cancer in a mammal. In a preferred embodiment mammals, preferably human, at high risk for cancer are prophylactically treated with the immunising composition of the invention. Examples of such mammals include, but are not limited to, humans with a family history of cancer.

When provided therapeutically, the immunising composition of the invention is provided to enhance the patient's own immune response to the cancer antigen present on the cancer or metastatic cancer.

In one embodiment of the invention, the peptides of the invention may be conjugated with lipoprotein or administered in liposomal form or with adjuvant.

In one embodiment, said immunising composition is a pharmaceutical composition.

In such embodiment, said immunising composition, for human use, comprises at least one antigen peptide as described here above or at least one antibody as described here above, together with one or more pharmaceutically acceptable carriers and, optionally, other therapeutic ingredients. The carrier(s) must be "acceptable" in the sense of being compatible with the other ingredients of the composition and not deleterious to the recipient thereof. The immunising compositions may conveniently be presented in unit dosage form and may be prepared by any method well-known in the pharmaceutical art.

Immunising compositions suitable for intravenous, intradermal, intramuscular, subcutaneous, or intraperitoneal administration conveniently comprise sterile aqueous solutions of the active agent with solutions which are preferably isotonic with the blood of the recipient. Such compositions may be conveniently prepared by dissolving solid active ingredient in water containing physiologically compatible substances such as sodium chloride (e.g. 0.1-2.0M), glycine, and the like, and having a buffered pH compatible with physiological conditions to produce an aqueous solution, and rendering said solution sterile. These may be present in unit or multi-dose containers, for example, sealed ampoules or vials.

The immunising compositions of the invention may incorporate a stabilizer. Illustrative stabilizers are polyethylene glycol, proteins, saccharides, amino acids, inorganic acids, and organic acids which may be used either on their own or as admixtures. These stabilizers are preferably incorporated in an amount of 0.11-10,000 parts by weight per part by weight of active agent. If two or more stabilizers are to be used, their total amount is preferably within the range specified above. These stabilizers are used in aqueous solutions at the appropriate concentration and pH. The specific osmotic pressure of such aqueous solutions is generally in the range of 0.1-3.0 osmoles, preferably in the range of 0.8-1.2. The pH of the aqueous solution is adjusted to be within the range of 5.0-9.0, preferably within the range of 6-8.

Additional pharmaceutical methods may be employed to control the duration of action. Controlled release preparations may be achieved through the use of polymer to complex or absorb the peptides of the invention. The controlled delivery may be exercised by selecting appropriate macromolecules (for example polyester, polyamino acids, polyvinyl, pyrrolidone, ethylenevinylacetate, methylcellulose, carboxymethylcellulose, or protamine sulfate) and the concentration of macromolecules as well as the methods of incorporation in order to control release. Another possible method to control the duration of action by controlled-release preparations is to incorporate the antigen peptides of the invention into particles of a polymeric material such as polyesters, polyamino acids, hydrogels, poly(lactic acid) or ethylene vinylaceiate copolymers. Alternatively, instead of incorporating these agents into polymeric particles, it is possible to entrap these materials in microcapsules prepared, for example, by coacervation techniques or by interfacial polymerization, for example, hydroxy-methylcellulose or gelatin-microcapsules and poly(methylmethacylate) microcapsules, respectively, or in colloidal drug delivery systems, for example, liposomes, albumin microspheres, microemulsions, nanoparticles, and nanocapsules or in macroemulsions.

When oral preparations are desired, the compositions may be combined with typical carriers, such as lactose, sucrose, starch, talc magnesium stearate, crystalline cellulose, methyl cellulose, carboxymethyl cellulose, glycerin, sodium alginate or gum arabic among others.

Immunisation of a subject with the immunising composition of the invention can be conducted by conventional methods, for example, in the presence of conventional adjuvants. Examples of conventional adjuvant include, but are not limited to, metal salts, oil in water emulsions, Toll like receptors agonists, saponins, lipid A, alkyl glucosaminide phosphate, Freund's adjuvant, keyhole limpet haemocyanin (KLH), mannan, BCG, alum, cytokines such as IL-1, IL-2, macrophage colony stimulating factor, and tumor necrosis factor; and other substances that act as immunostimulating agents such as muramyl peptides or bacterial cell wall components, toxins, toxoids and TLR ligands.

The immunising composition can be administered by any route appropriate for antibody production and/or T cell activation such as intravenous, intraperitoneal, intramuscular, subcutaneous, and the like. The immunising composition may be administered once or at periodic intervals until a significant titre of anti-Nectin4 immune cells or anti-Nectin4 antibody is produced. The presence of anti-Nectin4 immune cells may be assessed by measuring the frequency of precursor CTL (cytoxic T-lymphocytes) against the antigen peptides of the invention prior to and after immunization by specific tetramer labelling or by a CTL precursor analysis assay. The antibody may be detected in the serum using an immunoassay.

Antibodies directed to the antigens of the invention can also be used directly as anti-cancer agents. To prepare antibodies, a host animal may be immunized using the Nectin4 protein or others antigen peptides as described here above. The host serum or plasma is collected following an appropriate time to provide a composition comprising antibodies reactive to said antigen peptides. The gamma globulin fraction or the IgG antibodies can be obtained, for example, by use of saturated ammonium sulfate or DEAE Sephadex, or other techniques known to those skilled in the art. The antibodies are substantially free of many of the adverse side effects which may be associated with other anti-cancer agents such as chemotherapy.

The immunising composition of the invention comprising antibodies as described here above can be made even more compatible with the host system by minimizing potential adverse immune system responses. This is accomplished by removing all or a portion of the Fc portion of a foreign species antibody or using an antibody of the same species as the host subject, for example, the use of antibodies from human/human hybridomas. Humanized antibodies (i.e., nonimmunogenic in a human) may be produced, for example, by replacing an immunogenic portion of an antibody with a corresponding, but nonimmunogenic portion (i.e., chimeric antibodies). Such chimeric antibodies may contain the reactive or antigen binding portion of an antibody from one species and the Fc portion of an antibody (nonimmunogenic) from a different species. Examples of chimeric antibodies, include but are not limited to, nonhuman mammal-human chimeras, rodent-human chimeras, murine-human and rat-human chimeras.

Methods for obtaining said antibodies, chimeric antibodies and humanized chimeric antibodies are well-known in the art.

The immunising composition comprising the antibodies of the invention can also be used as a means of enhancing the immune response. The antibodies can be administered in amounts similar to those used for other therapeutic administrations of antibody. For example, pooled gamma globulin is administered at a range of about 1 mg to about 100 mg per subject. Thus, antibodies reactive with the antigen peptides of the invention can be passively administered alone or in conjunction with other anti-cancer therapies to a mammal afflicted with cancer. Examples of anti-cancer therapies include, but are not limited to, chemotherapy, radiation therapy, adoptive immunotherapy therapy with TIL.

The antibodies or chimeric antibodies described herein may also be coupled to toxin molecules, radioisotopes and drugs by conventional methods. Examples of toxins to which the antibodies may be coupled to included, but are not limited to, ricin or diphtheria toxin. Examples of drugs or chemotherapeutic agents include, but are not limited to, cyclophosphamide or doxorubicin. Examples of radioisotopes, include, but are not limited to, 131I. Antibodies covalently conjugated to the aforementioned agents can be used in cancer immunotherapy for treating cancer.

If the subject to be immunized is already afflicted with cancer or metastatic cancer, the immunising composition of the invention can be administered in conjunction with other therapeutic treatments. Examples of other therapeutic treatments includes, but are not limited to, adoptive T cell immunotherapy, coadministration of cytokines or other therapeutic drugs for cancer.

The dose of antigen peptide of the invention to be administered to a subject may be adjusted as appropriate depending on, for example, the disease to be treated, the age and the body weight of said subject. Ranges of antigen peptides of the invention that may be administered are about 0.001 to about 100 mg per subject, preferred doses are about 0.01 to about 10 mg per subject.

The immunising composition of the invention may be evaluated first in animal models, initially rodents, and in nonhuman primates and finally in humans. The safety of the immunization procedures is determined by looking for the effect of immunization on the general health of the immunized animal (weight change, fever, appetite behavior etc.) and looking for pathological changes on autopsies. After initial testing in animals, cancer patients can be tested. Conventional methods would be used to evaluate the immune response of the patient to determine the efficiency of the immunising composition.

Another object of the invention is an immunising composition comprising (a) at least one antigen peptide as described here above or (b) an expression vector comprising a nucleic acid sequence encoding a antigen peptide defined in (a) as described here above, or (c) a host cell comprising an expression vector defined in (b) as described here above, or (d) an antibody that recognizes specifically a antigen peptide defined in (a) as described here above, or (e) at least one nucleic acid encoding at least one antigen peptide of the invention, for preventing or treating cancer in a subject in need thereof.

In one embodiment, the cancer may be breast, ovarian or lung cancer.

Antigen Presenting Cell

Another object of the invention is an antigen presenting cell comprising a complex HLA antigen and an antigen peptide of the invention.

In one embodiment of the invention, said complex HLA antigen is a HLA-A*0201 antigen.

In one embodiment of the invention, said antigen presenting cell is derived from the subject to be treated.

The term "antigen presenting cell" (APCs) refers to any cell that expresses an HLA antigen capable of presenting the antigen peptide of the invention on its surface. Dendritic cells, which are reported to have an especially high antigen-presenting ability, are preferred.

In another embodiment, artificial APCs may also be used such mammalian cells (fibroblast, endothelial cells, keratinocytes), insect cells, or cell lines.

In order to prepare such APCs of the invention, cells having an antigen-presenting ability are isolated from the subject to be treated, and pulsed ex vivo with at least one antigen peptide of the invention to form a complex with the HLA-A*0201 antigen.

In case dendritic cells are used, the APC of the invention can be prepared as follows. Lymphocytes are isolated from peripheral blood of the subject to be treated by Ficoll method; adherent cells are separated from non-adherent cells; the adherent cells are then cultured in the presence of GM-CSF and IL-4 to induce dendritic cells; and the dendritic cells are pulsed by culturing with at least one antigen peptide of the invention to obtain the APCs of the invention. The dendritic cells should be exposed to the antigen peptide for sufficient time to allow the antigens to be internalized and presented on the dendritic cells surface. The resulting dendritic cells can then be re-administered to the subject to be treated. Such methods are described in WO93/208185 and EP0563485, which are incorporated by reference.

Another object of the invention is a composition for active immunotherapy comprising antigen presenting cells comprising a complex HLA antigen and an antigen peptide of the invention.

In one embodiment of the invention, said antigen presenting cells comprise a complex HLA-A*0201 antigen and a antigen peptide of the invention.

Said APCs may be preferably contained in physiological saline, phosphate buffered saline (PBS), culture medium, or the like. Administration may be achieved, for example, intravenously, hypodermically, or intradermally.

Lymphocytes T and Uses Thereof

Another object of the invention is a T lymphocyte that recognizes specifically the antigen peptide of the invention.

In one embodiment of the invention, said T lymphocyte is a cytotoxic T lymphocyte.

In another embodiment of the invention, said T lymphocyte is HLA-A*0201 restricted.

In another embodiment of the invention, said T lymphocyte is a T cell clone.

In another embodiment, said T lymphocyte is a genetically modified T lymphocyte that expresses a TCR that recognizes specifically the antigen peptide of the invention.

Another object of the invention is a composition for adoptive therapy comprising said T lymphocytes as described here above that recognizes specifically the antigen peptide of the invention.

In the case of cancer, and preferable in breast, ovarian or lung cancer, it has been observed that an adoptive immunotherapy wherein intratumoral T cell infiltrate taken from the subject to be treated are cultured ex vivo in large quantities, and then returned into the patient achieves a therapeutic gain.

It is preferred that the T cells are contained in physiological saline, phosphate buffered saline (PBS), culture medium, or the like in order to their stable maintain. Administration may be achieved, for example, intravenously or intra-tumoraly. By returning the T cells that recognizes specifically the antigen peptide of the invention into the subject's body, the toxicity of said T cells on tumor cells is enhanced in the patient who is positive for Nectin4. The tumor cells are destroyed and thereby the treatment of tumor is achieved.

Examples of where T-lymphocytes can be isolated, include but are not limited to, peripheral blood cells lymphocytes (PBL), lymph nodes, or tumor infiltrating lymphocytes (TIL).

Such lymphocytes can be isolated from tumor or peripheral blood of the individual to be treated by methods known in the art and cultured in vitro. Lymphocytes are cultured in media such as RPMI or RPMI 1640 for 2-5 weeks, preferably for 2-3 weeks. Viability is assessed by trypan blue dye exclusion assay. The lymphocytes are exposed to the antigen peptide of the invention for all of the culture duration.

In a preferred embodiment the lymphocytes are exposed to the antigen peptide of the invention at a concentration of about 1 to about 10 micrograms (μg)/ml per 107 cells for all the duration of lymphocyte culture. Cytokines may be added to the lymphocyte culture such as IL-2.

The antigen peptide of the invention may be added to the culture in presence of antigen presenting cells such as dendritic cells or allogeneic irradiated cancer cell line cells.

After being sensitized to the peptide, the T-lymphocytes are administered to the subject in need of such treatment.

Examples of how these sensitized T-cells can be administered to the mammal include but are not limited to, intravenously, intraperitoneally or intralesionally. Parameters that may be assessed to determine the efficacy of these sensitized T-lymphocytes include, but are not limited to, production of immune cells in the subject being treated or tumor regression. Conventional methods are used to assess these parameters. Such treatment can be given in conjunction with cytokines or gene modified cells (Rosenberg, S. A. et al. (1992) Human Gene Therapy, 3: 75-90; Rosenberg, S. A. et al. (1992) Human Gene Therapy, 3: 57-73).

Another object of the invention is a method for producing T lymphocytes that recognize specifically an antigen peptide of the invention, said method comprising the steps of:
(a) stimulating peripheral blood mononuclear cells (PBMCs) or tumor infiltrating lymphocytes (TIL) obtained from a subject with at least one antigen peptide of the invention,
(b) enriching the population of T lymphocytes specific for the antigen peptide(s) used in (a),
(c) optionally cloning said population of T lymphocytes specific for the antigen peptide(s) used in (a).

Enrichment and/or cloning may be carried out by using an MHC/peptide multimer as described here above. Cloning may also be carried out by conventional methods.

In one embodiment of the invention, the T lymphocytes that recognize specifically an antigen peptide of the invention are HLA-A*0201 restricted. In such embodiment, enrichment and/or cloning may be carried out by using an HLA-A*0201/peptide multimer as described here above.

Stimulation of PBMCs may be carried out with at least one antigen peptide of the invention alone, or presented by an antigen presenting cell such as dendritic cells or allogeneic irradiated cancer cell line cells. Typically, cytokines such as IL-2 may also be added to the culture.

Another object of the invention is a composition for adoptive therapy that comprises lymphocytes that recognizes specifically the antigen peptide of the invention for preventing or treating cancer in a subject in need thereof, wherein said T lymphocytes are to be re-administered to the subject.

In one embodiment, the cancer may be breast, ovarian or lung cancer.

In one embodiment, said lymphocytes that recognizes specifically the antigen peptide of the invention are HLA-A*0201 restricted.

The invention also relates to a method for treating cancer in a subject in need thereof, comprising administering a therapeutically effective amount of (a) at least one antigen peptide as described here above or
(b) an expression vector as described here above, or
(c) a host cell as described here above, or
(d) an antibody as described here above, or
(e) at least one nucleic acid encoding at least one antigen peptide of the invention.

The invention also relates to a method for treating cancer in a subject in need thereof, comprising administering a therapeutically effective amount of T lymphocytes that recognizes specifically the antigen peptide of the invention. In one embodiment, said T lymphocytes are HLA-A*0201 restricted.

The invention also relates to a method for treating cancer in a subject in need thereof, comprising administering a therapeutically effective amount of antigen presenting cells comprising a complex HLA antigen and a antigen peptide of the invention. In one embodiment, said complex HLA/peptide is a complex HLA-A*0201/antigen peptide of the invention.

Monitoring Assay

Another object of the invention is a method for monitoring a cancer, especially an ovarian, breast or lung cancer in a subject in need thereof, comprising determining the frequency of T lymphocytes that recognize specifically a antigen peptide of the invention.

In one embodiment of the invention, said T lymphocytes are HLA-A*0201 restricted.

In one embodiment of the invention, the frequency of T lymphocytes that recognize specifically an antigen peptide of the invention may be determined by using an MHC/peptide multimer as described here above.

According to the invention, an increase in the frequency of T lymphocytes that recognize specifically an antigen peptide of the invention correlates with relapse prevention.

Kit

Another object of the invention is a kit comprising:
an antibody that recognizes specifically the antigen peptide and/or
primers or probes for Nectin4 mRNA detection, and/or
an MHC/peptide multimer comprising a antigen peptide of the invention.

In one embodiment, said kit further comprises a solid support, wherein said solid support is selected from the group consisting of wells of reaction trays, test tubes, polystyrene beads, strips, membranes and microparticles.

In another embodiment, said kit further comprises a label, wherein said label is selected in the group consisting of enzymes, radioisotopes, fluorescent compounds and chemiluminescent compounds.

The invention will be further illustrated by the following figures and examples. However, these examples and figures should not be interpreted in any way as limiting the scope of the present invention.

FIGURES

FIG. 1: Frequency of peptide binding to 8 HLA alleles. The 502 nonamers overlapping by 8 aa, were tested in the iTOPIA EDS system. Cut-off values were as defined by the manufacturer.

FIG. 2: Off-rates and binding curves for selected peptides binding HLA-A*0201.

The number associated with peptides represent where the peptide starts in the protein sequence. Curves are fitted using the GRAPHPAD's Prism software (a scientific 2D graphing and statistics software). A: Peptide titration curves for selected nectin4 peptides, B: Peptide titration curves for reference peptides, C: Off-rate curves for selected nectin4 peptide, D: Off-rate curves for reference peptides.

FIG. 3: HLA stabilization assay using the CEMT2 cell line was assessed by flow cytometry. Examples of binding and dissociation histograms of Nectin4 and HBV positive control.

Binding of peptide 145 (white histogram), peptide 122 (grey histogram) or no peptide (dotted histogram) (A) and HBV positive control peptide (white histogram) (B). Kinetic of dissociation for peptide 145 (C) and HBV positive control peptide (D). T0h (solid line), T1h (dotted line), T4h (dashed line), peptide 122 (grey histogram).

FIG. 4: Characterization of anti-nectin4 CTL derived from healthy PBMC donors.

Labeling of CTL 21 and CTL 145 with HLA-A2/Nectin4 tetramers loaded with peptide 21 (SEQ ID NO: 17) (A) and peptide 145 (SEQ ID NO: 2) (B). CTL 21 and CTL 145 mediated lysis of HLA-A2 nectin4 negative MDA-MB-231 target cells loaded or not with Nectin4 peptide 21 (C, left) or peptide 145 (D, left) respectively. CTL 21 and CTL 145 mediated lysis of HLA-A2 nectin4 expressing MDA-MB-231 target cells loaded or not with Nectin4 peptide 21 (C, right) or peptide 145 (D, right) respectively.

Figure 5:
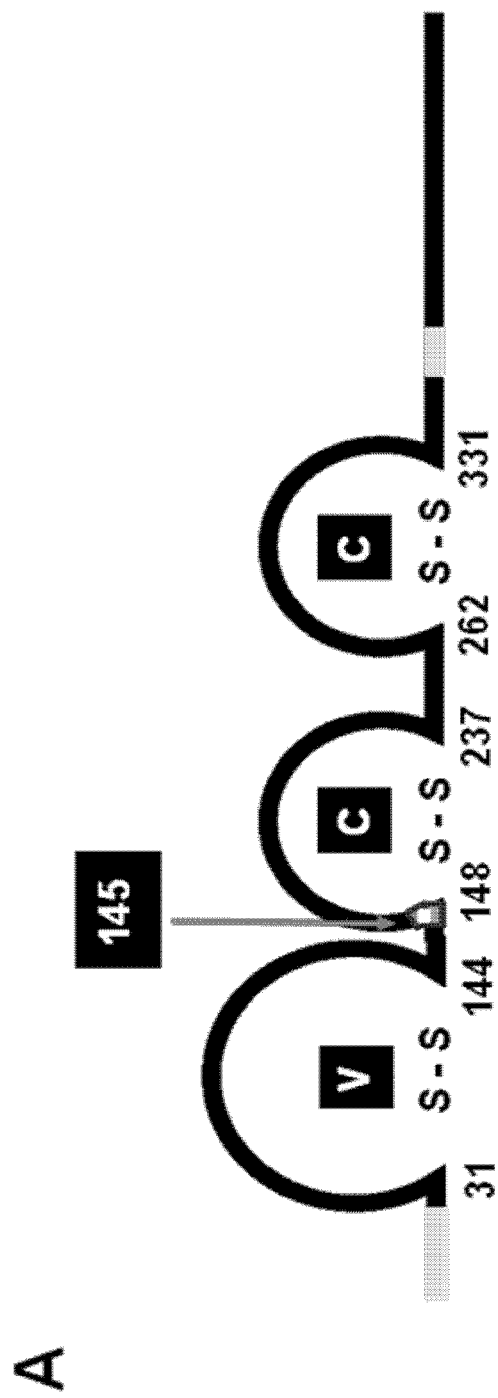

FIG. 5: Characteristics of N4-145 peptide.

A: Nectin4 is a type-I transmembrane glycoprotein that belongs to the immunoglobulin superfamily. Nectin4 exhibits 3 Ig-like domains of V, C, C type in the extracellular region. Peptide N4-145 localized at the edge of the second Ig-like type C domain. Transmembrane region is in grey. B: Characteristics of N4-145 peptide for the 8 different HLA alleles.

TABLE 1

List of control peptides used in the study.

| Peptide N° | Sequence | Origin | SEQ ID NO |
|---|---|---|---|
| 503 | NLSASVATV | Proteinase3 | 3 |
| 513 | SLLMWITQV | NY-ESO-1 | 4 |
| 514 | LYVDSLFFL | PRAME | 5 |
| 515 | KVAELVHFL | MAGE-A3 | 6 |
| 516 | ASSTLYLVF | MAGE-C2 | 7 |
| 517 | GLYDGMEHL | MAGE-A10 | 8 |
| 518 | ALKDVEERV | MGAE-C2 | 9 |
| 519 | YMDGTMSQV | Tyrosinase | 10 |
| 520 | VLPDVFIRC | GnTV | 11 |

All these peptides have been referenced and validated as naturally processed and recognized by specific CTL. Some of these control peptides are used in pre-clinical or clinical settings. These peptides were selected to compare with selected nectin4 peptides in the different assays.

TABLE 2

Selection and binding characteristics of the 22 high rank HLA-A2 nectin4 peptides based on iTOPIA analysis.

| Rank | Peptide N° | SEQ ID NO | Sequence | % Binding | T½ Value (Hours) | Affinity (ED50) | iScore |
|---|---|---|---|---|---|---|---|
| 1 | 238 | 12 | HILHVSFLA | 87 | 6.7 | 6,00E-08 | 1.426 |
| 2 | 355 | 13 | VIAALLFCL | 59 | 5.2 | 3,00E-08 | 0.888 |
| 3 | 354 | 14 | GVIAALLFC | 61 | 6.2 | 9,00E-08 | 0.845 |
| 4 | 80 | 15 | ALLHSKYGL | 87 | 7.8 | 1,00E-06 | 0.815 |
| 5 | 351 | 16 | VVVGVIAAL | 58 | 3.4 | 3,00E-08 | 0.784 |
| 6 | 145 | 2 | VLVPPLPSL | 67 | 7.4 | 5,00E-07 | 0.783 |
| 7 | 21 | 17 | LLASFTGRC | 91 | 6 | 6,00E-07 | 0.727 |
| 8 | 358 | 18 | ALLFCLLVV | 53 | 6.1 | 2,00E-07 | 0.71 |
| 9 | 347 | 19 | SASVVVVGV | 64 | 3.7 | 2,00E-07 | 0.708 |
| 10 | 215 | 20 | SMNGQPLTC | 81 | 6.8 | 7,00E-07 | 0.689 |
| 11 | 359 | 21 | LLFCLLVVV | 67 | 7.4 | 5,00E-07 | 0.674 |
| 12 | 266 | 22 | AMLKCLSEG | 74 | 6.8 | 7,00E-07 | 0.667 |
| 13 | 137 | 23 | FQARLRLRV | 69 | 7.3 | 8,00E-07 | 0.66 |
| 14 | 19 | 24 | LLLLASFTG | 75 | 2.1 | 6,00E-08 | 0.659 |
| 15 | 345 | 25 | LVSASVVVV | 51 | 2.3 | 6,00E-08 | 0.626 |
| 16 | 357 | 26 | AALLFCLLV | 56 | 3.8 | 1,00E-07 | 0.619 |
| 17 | 35 | 27 | GTSDVVTVV | 63 | 2.9 | 3,00E-07 | 0.539 |
| 18 | 255 | 28 | DQNLWHIGR | 62 | 5.4 | 5,00E-07 | 0.539 |
| 19 | 244 | 29 | FLAEASVRG | 78 | 2.8 | 7,00E-07 | 0.533 |
| 20 | 203 | 30 | AVTSEFHLV | 64 | 3.5 | 4,00E-07 | 0.533 |
| 21 | 443 | 31 | RSYSTLTTV | 68 | 2.4 | 3,00E-07 | 0.521 |
| 22 | 239 | 32 | ILHVSFLAE | 61 | 2.3 | 2,00E-07 | 0.51 |

TABLE 3

Summary of iTOPIA, CEM T2, SYFPEITHI and BIMAS data obtained for the 22 Nectin4 peptides with iScore ≥0.50.

| Peptide N° | Sequence | SEQ ID NO | i-TOPIA iScore | CEM.T2 % Binding | CEM.T2 % Residual Binding | Algorithms SYFPEITHI | Algorithms BIMAS |
|---|---|---|---|---|---|---|---|
| 19 | LLLLASFTG | 24 | 0.659 | 17 | 0 | 16 | 2 |
| 21 | LLASFTGRC | 17 | 0.727 | 44 | 86 | 17 | 4 |
| 35 | GTSDVVTVV | 27 | 0.539 | 60 | 0 | 20 | 3 |
| 80 | ALLHSKYGL | 15 | 0.815 | 53 | 86 | 26 | 79 |
| 137 | FQARLRLRV | 23 | 0.66 | 30 | 72 | 13 | 32 |
| 145 | VLVPPLPSL | 2 | 0.783 | 76 | 54 | 31 | 83 |
| 203 | AVTSEFHLV | 30 | 0.533 | 48 | 0 | 16 | 11 |

TABLE 3-continued

Summary of iTOPIA, CEM T2, SYFPEITHI and BIMAS data obtained for the 22 Nectin4 peptides with iScore ≥0.50.

| Peptide N° | Sequence | SEQ ID NO | i-TOPIA iScore | CEM.T2 % Binding | CEM.T2 % Residual Binding | Algorithms SYFPEITHI | Algorithms BIMAS |
|---|---|---|---|---|---|---|---|
| 215 | SMNGQPLTC | 20 | 0.689 | 21 | 0 | 16 | 3 |
| 238 | HILHVSFLA | 12 | 1.426 | 37 | 66 | 14 | 0 |
| 239 | ILHVSFLAE | 32 | 0.51 | 10 | 0 | 14 | 0 |
| 244 | FLAEASVRG | 29 | 0.533 | 12 | 0 | 17 | 1 |
| 255 | DQNLWHIGR | 28 | 0.539 | 6 | 0 | 1 | 0 |
| 266 | AMLKCLSEG | 22 | 0.667 | 31 | 39 | 18 | 0 |
| 345 | LVSASVVVV | 25 | 0.626 | 11 | 0 | 22 | 9 |
| 347 | SASVVVVGV | 19 | 0.708 | 40 | 0 | 23 | 2 |
| 351 | VVVGVIAAL | 16 | 0.784 | 82 | 50 | 24 | 7 |
| 354 | GVIAALLFC | 14 | 0.845 | 10 | 0 | 12 | 5 |
| 355 | VIAALLFCL | 13 | 0.888 | 18 | 24 | 26 | 66 |
| 357 | AALLFCLLV | 26 | 0.619 | 15 | 18 | 20 | 13 |
| 358 | ALLFCLLVV | 18 | 0.71 | 26 | 26 | 28 | 242 |
| 359 | LLFCLLVVV | 21 | 0.674 | 7 | 23 | 30 | 412 |
| 443 | RSYSTLTTV | 31 | 0.521 | 37 | 0 | 17 | 3 |

TABLE 4

Ranking of the best five nectin4 peptides selected on the basis of the F-score (iTOPIA and CEM T2). Comparison with reference peptides listed in table 1.

| RANK F-Score | N° Peptide | SEQ ID NO |
|---|---|---|
| 1 | 520 (GnTV) | 11 |
| 2 | 513 (NY-ESO-1) | 4 |
| 3 | 519 (Tyrosinase) | 10 |
| 4 | 80 | 15 |
| 5 | 351 | 16 |
| 6 | 145 | 2 |
| 7 | 238 | 12 |
| 8 | 517 (MAGE-A10) | 8 |
| 9 | 503 (PR3) | 3 |
| 10 | 515 (MAGE-A3) | 6 |
| 11 | 21 | 17 |

EXAMPLE

Material & Methods

Cell Lines

MDA-MB-231 breast carcinoma cell line (ATCC, Manassas) was cultivated in DMEM supplemented with 10% fetal calf serum, 50 IU/ml penicillin, 50 μg/ml streptomycin, and 2 mM glutamine. Cells were cultivated in a 5% $CO_2$ atmosphere at constant humidity. The MDA-MB-231 nectin4 cell line was obtained after transfection with the p3XFLR4.C1 [S. Fabre et al, 2002].

The Epstein Barr Virus-transformed B (EBV-B) cell lines were cultured in IMDM supplemented with 10% fetal calf serum, with 0.24 mM L-asparagine, 0.55 mM L-arginine, 1.5 mM L-glutamine (AAG), 100 U/ml penicillin and 100 μg/ml streptomycin. Human recombinant IL-2 was purchased from Novartis. Human recombinant IL-4, IL-7 and GM-CSF were from R&D Systems, MN, USA.

Peptides

A library of 502 nonapeptides which span the entire 510 amino acid sequence of human nectin4, was synthesized (JPT Peptide Technologies GmbH, Berlin Germany). A series of 9 peptides described in the literature was selected and used as reference (Table 1). Peptides (purity >80%) were dissolved in DMSO at a concentration of 10 mM and stored at −20° C. Specific control peptides for each allele were supplied by the manufacturer of the iTOPIA Epitope Discovery System (EDS) (Beckman Coulter Inc., San Diego, Calif., USA). The 502 peptides were tested for binding to eight alleles (HLA-A*0101; HLA-A*0201; HLA-A*0301; HLA-A*1101; HLA-A*2402; HLA-A*0702; HLA-B*0801; HLA-B*1501) with the iTOPIA EDS.

MHC peptide binding assay using iTOPIA EDS

Microtiter 96 well plates containing HLA class I MHC monomer loaded with the human β2-microglobulin and a "placeholder" peptide were used to evaluate peptide binding, affinity, and off-rate.

The 502 nectin4 nonapeptides were first evaluated for their ability to bind to each MHC molecule in the peptide binding assay. In this assay, the placeholder peptides were stripped from the MHC class I monomer complexes coated on plastic, which leaves the MHC class I heavy chain available as a binding partner for candidate peptides in the presence of human β2-microglobulin.

Peptide binding was performed at 21° C. for 18 h. Revelation was done using an anti HLA-ABC-FITC mAb that binds to refolded MHC complex conformation. The relative fluorescent intensity was read using a fluorimeter (Molecular Devices, SpectraMax Gemini, Sunnyvale, Calif., USA).

Peptides with a binding>30% of the positive control peptide were selected as "binder" and subsequently analyzed for affinity (ED50) and off-rate (T1/2).

Off-Rate Assay

This assay evaluates the dissociation rate of "binder" peptides as a function of time. As for binding assay, peptides were incubated with MHC class I monomer at 21° C. for 18 h. Plates were then incubated at 37° C. and the MHC classI/peptide/β2-microglobulin complex was measured at 0.5, 1, 1.5, 2, 4, 6, 8 hours under agitation. The t1/2 value corresponds to the time in hours required to reach a 50% reduction of fluorescence intensity, i.e., a 50% of complex dissociation.

Affinity Assay

"Binder" peptides were incubated with MHC class I monomer at 21° C. for 18 h at concentrations ranging from $10^{-4}$ to $10^{-9}$ M. Affinity (ED50 value) is expressed as the peptide concentration that gives 50% of the optimal binding.

iScore Calculation

The iTOPIA system software was used to include, binding, off-rate (T1/2 value) and affinity (ED50 value) data collected for each peptide, in a multiparametric score called iScore. The corresponding graphs were generated using the GRAPHPAD Prism®. Peptides with iScore >0.50 were considered as good candidates for HLA A*0201 binding.

Cellular Binding Assay

The CEM.T2 cell line (T2) is defective in the processing of proteins for presentation by MHC class 1 molecules. This cell line expresses HLA A*0201 but is deficient for TAP transporter. T2 is classically used to assess the Peptide/HLA-A*0201 Complex Stability[H. W. Nijman et al., 1993]

For HLA-A2*0201 stabilization, T2 cells (2×105/well) were incubated in serum-free RPMI (Gibco®-France) with 100 μM of selected peptide, at 37° C. for 4 h. Cells were washed two times with PBS supplemented with 1% BSA and stained with fluorescein isothiocyanate-conjugated anti HLA-A2 (Clone BB7.2) (BD Bioscience Pharmingen-France-) at 4° C. for 45 min. After 3 washes, cells were fixed in PBS supplemented with 2% paraformaldehyde and analyzed by FACS (FACScan, BD Bioscience). The percentage of peptide binding was calculated as follows:

% Binding={(MFI peptide sample−MFI Neg control)/
(MFI Pos control−MFI Neg control)}×100

The peptide FLPSDFFPSV from Hepatitis B Virus [I. A. Doytchinova et al., 2004] was used as positive control peptide. Negative control was done without peptide.

Cellular Dissociation Assay

After HLA-A2*0201 stabilization with peptides at 37° C. for 4 h, T2 cells were incubated for 1 h, in serum-free RPMI containing Brefeldin A (10 μg/ml), an inhibitor of the transport of secretory and lysosomal proteins [G. J. Strous et al., 1993]. After 3 washes, T2 cells were incubated for 3 h in serum-free RPMI at 37° C. Binding was then measured by FACS and after 4 h incubation. Percentage of Residual Binding (% RB) was calculated as follows:

$$\%RB = \frac{100 - (MFI_{peptide\ sample} - MFI_{Neg\ control})_{T0} - (MFI_{peptide\ sample} - MFI_{Neg\ control})_{T4}}{(MFI_{Pos\ control} - MFI_{Neg\ control})_{T0} - (MFI_{Pos\ control} - MFI_{Neg\ control})_{T4}} \times 100$$

Multimer Production

Recombinant HLA-A*0201 molecules were folded in vitro with β2-microglobulin and nectin4 peptides and the EBV lytic cycle antigen BMLF1 peptide; VSDGGPNLY (SEQ ID NO: 33) [M. DiBrino, et el., 1993]. Purification was achieved by gel Titration. Biotinylated tetramers were then labeled with either Extravidin-PE (Sigma, St Louis, Mont., USA) for the HLA-A2/Nectin4 multimers, or streptavidin-APC (Molecular Probes, Eugen, Oreg., USA) for the HLA-A2/EBV multimer control.

Generation and Stimulation of Dendritic Cells

PBMC from HLA-A2+ healthy volunteers were isolated by Ficoll-Plaque density gradient centrifugation. To generate autologous dendritic cells, PBMC were left to adhere for 1 h at 37° C. in culture flasks in RPMI 1640 supplemented with L-Arginine, L-Asparagine L-Glutamine (AAG), 1% streptomycin/penicillin and 10% FBS (complete RPMI medium). Non-adherent cells were removed and cultivated in IMDM supplemented with AAG, 1% streptomycin/penicillin, 10% human serum and IL-2 (5 U/ml) for 6 days. Adherent-cells were cultured in presence of GM-CSF (70 ng/ml) and IL-4 (200 U/ml) in complete RPMI medium. Cultures were fed on days 2 and 4 by removing 1/3 of the volume and adding fresh medium with cytokines.

Autologous monocyte-derived immature dendritic cells were incubated for 6 h with 10 μg/ml of a nectin4 peptide pool comprising LLASFTGRC (SEQ ID NO: 17; Pep N° 21), ALLHSKYGL (SEQ ID NO: 15; Pep N° 80), VLVPPLPSL (SEQ ID NO: 2; Pep N° 145), VVVGVIAAL (SEQ ID NO: 16; Pep N° 351), IL-4 (200 U/ml), GM-CSF (70 ng/ml), in presence of 1 μg/ml of Immucytal® granulare (Pierre Fabre Medicament Production, Gien, France) and 500 U/ml of INF-γ (R&D Systems). Dendritic cells were used to sustain activation of sorted lymphocytes.

Isolation of CTL Populations

Non-adherent cells (10×10$^8$ cells/ml) were incubated for 15 min at room temperature with HLA-A2 multimers loaded with Nectin4 peptides (20 nM).

Multimer-labeled cells were incubated at 4° C. with anti-PE microbeads as recommended by the manufacturer (Miltenyi Biotec, Bergisch-Gladbach, Germany). After three washes, cells were magnetically sorted by AUTOMACS™ (Miltenyi Biotec). Efficacy of cell sorting was measured on a FACS CANTO™ II (Becton-Dickinson, Calif., USA). Sorted cells were incubated in 96 U-bottomed plates (2×104/200 μl) in IMDM medium containing IL-2 (20 U/ml), IL-7 (10 ng/ml) and 1.104 peptide pulsed irradiated autologous dendritic cells [S. Ottaviani, et al., 2005].

Cytotoxicity Assay

CTL cells were tested for cytolytic activity against the indicated target cells in a 4 h $^{51}$Cr-release assay as previously described [C. Bottino et al., 2001]. The E/T ratios are indicated in the text.

Results

Identification of Nectin4 Peptides that Bind MHC Class I Alleles.

Nectin4 protein is a 510 aminoacids long protein. Screening of 502 nectin4 nonapeptides, spanning the entire sequence, was carried out on 8 different alleles (HLA-A*0101; HLA-A*0201; HLA-A*0301; HLA-A*1101; HLA-A*2402; HLA-A*0702; HLA-B*0801; HLA-B*1501) using the iTOPIA EDS. Peptide binding was analyzed according to manufacturer recommendations, i.e., with an arbitrary cut-off of 30% relative to the binding of allele specific control peptides. The number of positive peptides over 502 tested was represented for each allele in FIG. 1. We identified 5 HLA-A*0101, 130 HLA-A*0201, 24 HLA-A*0301, 38HLA-A*1101, 77 HLA-A*2402, 28 HLA-B*0702, 14 HLA-B*0801, 40 HLA-B*1501 binding peptides. Percentage of binding peptides ranged from 1% for HLA-A*0101 to 25% for HLA-A*0201.

Interestingly, we found that the greatest rates of peptides binding are in HLA-A*0201, HLA-A*2402 and HLA-B*1501 with respectively 130, 77, 40 positive peptides. These alleles have the similar binding motif. We decided to focus our study on HLA-A*0201 which represents the most frequent allele in US and Caucasian populations. As shown, in FIG. 1, we found 130 nectin4 peptides with relative binding affinity higher than 30% of HLA-A*0201 positive control peptides. In order to select the best "binders", the cut-off value was increased to 50% and 63 peptides were selected for the study.

Determination of Off-Rate Stability and Binding Affinity of the Selected Nectin4 Peptides.

Analysis of binding affinity revealed that the peptides 21, 80, 145 present affinity close to the positive control peptide (POS) (FIG. 2A) and better than the selected reference TAA peptides (FIG. 2B). Indeed, over a peptide concentration ranging from $10^{-4}$ to $10^{-9}$ M, the estimated dose to reach 50% maximal binding (ED50) was around $10^{-7}$ M for these three peptides.

The relative stability of each complex was evaluated for a period of 8 h as described in material and methods. Off-rate stability was determined by measuring the dissociation time of the complex (t1/2). Three groups were found according to the t1/2 value. Among the 63 peptides, 16 have a t1/2>4 h, 19 a t1/2 between 2 h and 4 h, and 28 a t1/2<2 h. Decay curves are represented in FIGS. 2C and 2D. t1/2 of five representative nectin4 peptides is showed and compared with the positive control peptide (POS) (FIG. 2C) and the reference peptides listed in table 1 (FIG. 2D). Among the 16 peptides with a t1/2 greater than 4 h, we found 3 nectin4 peptides (21, 80, 145) with a t1/2 over 6 hours. These values are close to the t1/2 of the positive control peptide and the reference peptides 513, 517, 519 (FIGS. 2C and 2D). Peptide 351 (t1/2=3.4 h) and peptide 229 (t1/2=1.7 h) represent peptides with intermediate and low off-rate stability, respectively.

The iScore is dedicated to define the overall peptide binding properties to HLA alleles. This multiparametric analysis includes binding, off-rate and affinity of the peptide/HLA complex. The 63 peptides studied for HLA-A*0201 were classified in three groups according to manufacturer recommendations: the first group including 23 peptides with a low iScore<0.25; the second group including 18 peptides with a iScore between 0.25 and 0.50; the third group includes 22 peptides with an iScore≥0.50. These 22 Nectin4 peptides can be considered as "good binders" (Table 2).

T2 Cell Binding and Dissociation Assay.

Because T2 cells lack TAP molecules, the HLA-A*0201 class I level on the cell surface of T2 cells is low. In the presence of binding peptides, HLA-A*0201 class I is stabilized, leading to up-regulation on the cell surface. This assay is highly relevant to peptide association with MHC class I molecule. However, this assay cannot be used for large screening. For this reason, we first restricted analysis on the 22 HLA-A*0201 class I binding peptides selected from iTOPIA assay (Table 2). As shown in FIG. 3A, the peptide 145 (white histogram) leads to increase the HLA-A*0201 class I level on T2 cells. The peptide 122, with a low iScore, does not increase HLA level on T2 cells (FIG. 3A, grey histogram). Positive control HBV peptide stabilized as well as peptide 145 (FIG. 3B, white histogram). In addition, dissociation assay was performed in the presence of Brefeldin A as described in material and methods. This assay is exemplified in FIGS. 3C and 3D for peptide 145 and control HBV peptide, respectively. Among the 22 peptide tested, peptides 80, 145, 351 have a binding score higher than 50% of positive control and a high residual binding. Overall T2 assay results are presented in table 3.

Integration of Overall Results: Ranking of Nectin4 Epitopes.

Table 3 presents the different score related to the 22 selected peptides i.e. the iScore obtained with iTOPIA EDS, the T2 assay results that integrate T2 binding and T2 dissociation results and the SYFPEITHI and BIMAS score.

Overall ranking of each peptide according to iTOPIA and cellular assays (F-Score) is shown in table 4. Ranking also includes control reference peptides presented in table 1. Peptides 80, 351, 145, 238 are ranked to the 4th, 5th, 6th, 7th position respectively. These peptides present binding characteristics close to the well characterized GnTV, NY-ESO-1 and tyrosinase peptides used in clinics.

Generation and Detection of CTL Clones with HLA-A*0201 Tetramers Folded with Nectin4 Peptides According to the above results, we then developed an approach to characterize functional anti-nectin4 CTL from PBMC of normal donors. Phycoerythrin (PE) labeled HLA-A*0201/nectin4 tetramers were used to select specific CTL by immunomagnetic cell sortings. After 21 days of culture, cells were screened with PE labeled tetramers (for example see FIGS. 4A and 4B). Tetramer-positive cells were tested for their capacity to kill nectin4 expressing tumor cells. Four out of five peptides selected and presented in table 4 were tested (80, 351, 145, 21). We used the MDA-MB-231 breast carcinoma cell line, which is HLA-A*0201 and does not express nectin4 as well as the MDA-MB-231 cell line transfected with Nectin4 plasmid. All the CTL isolated from the different tetramer/peptide were able to lyse the cell line when loaded with the respective peptides (see example FIG. 4C). Among the five different CTL, only the CTL isolated from HLA-A2/nectin4-145 peptide were able to kill the MDA-MB-231 cell line expressing nectin4 but not the wild-type MDA-MB-231 cells (FIG. 4D). These results lead to the identification of a naturally processed and HLA-A2 presented nectin4 peptide recognized by CD8+T lymphocytes. Peptide 145 sequence (SEQ ID NO: 16; VLVPPLPSL) is located at the beginning of the second Ig-like domain (FIG. 5A). Interestingly, iTOPIA EDS and SYFPEITHI analyzes highlight that this peptide behave as a "strong binder" candidate for HLA-A*0201, HLA-A*2402, HLA-B*1501 (FIG. 5B). This is of first importance regarding its potential use in clinical trials.

REFERENCES

Throughout this application, various references describe the state of the art to which this invention pertains. The disclosures of these references are hereby incorporated by reference into the present disclosure.

A. Takano et al., "Identification of nectin-4 oncoprotein as a diagnostic and therapeutic target for lung cancer," Cancer Research, vol. 69, n°. 16, p. 6694-6703, Aoû. 2009.

C. Bottino et al., "NTB-A [correction of GNTB-A], a novel SH2D1 A-associated surface molecule contributing to the inability of natural killer cells to kill Epstein-Barr virus-infected B cells in X-linked lymphoproliferative disease," *The Journal of Experimental Medicine*, vol. 194, n°. 3, p. 235-246. 2001.

D. Pende et al., "PVR (CD155) and Nectin-2 (CD112) as ligands of the human DNAM-1 (CD226) activating receptor: involvement in tumor cell lysis," Molecular Immunology, vol. 42, n°. 4, p. 463-469, Fey. 2005.

F. Brancati et al., "Mutations in PVRL4, encoding cell adhesion molecule nectin-4, cause ectodermal dysplasia-syndactyl)-syndrome," American Journal of Human Genetics, vol. 87, n°. 2, p. 265-273, Aoû. 2010.

G. J. Strous, P. van Kerkhof, G. van Meer, S. Rijnboutt, et W. Stoorvogel, "Differential effects of brefeldin A on transport of secretory and lysosomal proteins," The Journal of Biological Chemistry, vol. 268, n°. 4, p. 2341-2347, Fév. 1993.

H. W. Nijman et al., "Identification of peptide sequences that potentially trigger HLA-A2.1-restricted cytotoxic T lymphocytes," European Journal of Immunology, vol. 23, n°. 6, p. 1215-1219, Juin. 1993.

I. A. Doytchinova, V. A. Walshe, N. A. Jones, S. E. Gloster, P. Borrow, et D. R. Flower, "Coupling in silico and in vitro analysis of peptide-MHC binding: a bioinformatic approach enabling prediction of superbinding peptides and anchorless epitopes," Journal of Immunology (Baltimore, Md.: 1950), vol. 172, n°. 12, p. 7495-7502, Juin. 2004.

M. DiBrino, T. Tsuchida, R. V. Turner, K. C. Parker, J. E. Coligan, et W. E. Biddison, "HLA-A1 and HLA-A3 T cell epitopes derived from influenza virus proteins predicted from peptide binding motifs," Journal of Immunology (Baltimore, Md.: 1950), vol. 151, n°. 11, p. 5930-5935, Déc. 1993.

M. Kuramochi et al., "TSLC1 is a tumor-suppressor gene in human non-small-cell lung cancer," Nature Genetics, vol. 27, n°. 4, p. 427-430, Avr. 2001.

N. Reymond, S. Fabre, E. Lecocq, J. Adelaide, P. Dubreuil, et M. Lopez, "Nectin4/PRR4, a new afadin-associated member of the nectin family that trans-interacts with nectin1/PRR1 through V domain interaction," The Journal of Biological Chemistry, vol. 276, n°. 46, p. 43205-43215, November 2001.

N. Reymond et al., "DNAM-1 and PVR regulate monocyte migration through endothelial junctions," The Journal of Experimental Medicine, vol. 199, n°. 10, p. 1331-1341, Mai. 2004.

S. Fabre-Lafay et al., "Nectin-4 is a new histological and serological tumor associated marker for breast cancer," BMC Cancer, vol. 7, p. 73, 2007.

S. Fabre-Lafay, S. Gamido-Urbani, N. Reymond, A. Gonçalves, P. Dubreuil, et M. Lopez, "Nectin-4, a new serological breast cancer marker, is a substrate for tumor necrosis factor-alpha-converting enzyme (TACE)/ADAM-17," The Journal of Biological Chemistry, vol. 280, n°. 20, p. 19543-19550, Mai. 2005.

S. Fabre et al., "Prominent role of the Ig-like V domain in trans-interactions of nectins. Nectin3 and nectin 4 bind to the predicted C-C'-C"-D beta-strands of the nectin1 V domain," The Journal of Biological Chemistry, vol. 277, n°. 30, p. 27006-27013, Juil. 2002.

S. Ottaviani, Y. Zhang, T. Boon, et P. van der Bruggen, "A MAGE-1 antigenic peptide recognized by human cytolytic T lymphocytes on HLA-A2 tumor cells," Cancer Immunology, Immunotherapy: CII, vol. 54, n°. 12, p. 1214-1220, Déc. 2005.

Y. Takai et H. Nakanishi, "Nectin and afadin: novel organizers of intercellular junctions," Journal of Cell Science, vol. 116, n°. 1, p. 17-27, January 2003.

Y. Takai, W. Ikeda, H. Ogita, et Y. Rikitake, "The immunoglobulin-like cell adhesion molecule nectin and its associated protein afadin," Annual Review of Cell and Developmental Biology, vol. 24, p. 309-342, 2008.

Y. Takai, J. Miyoshi, W. Ikeda, et H. Ogita, "Nectins and nectin-like molecules: roles in contact inhibition of cell movement and proliferation," Nature Reviews. Molecular Cell Biology, vol. 9, n°. 8, p. 603-615, Aoû. 2008.

---

The invention claimed is:

1. A genetically modified T lymphocyte that recognizes specifically an antigen peptide in complex with human leukocyte antigen A2 (HLA-A2), wherein said antigen peptide comprises an amino acid motif having the amino acid sequence:

VLVPPLPSL (SEQ ID NO: 2).

2. A composition for adoptive therapy comprising a T lymphocyte according to claim 1.

* * * * *